(12) United States Patent
Ekman-Gunn et al.

(10) Patent No.: US 12,239,730 B2
(45) Date of Patent: Mar. 4, 2025

(54) LEAVE-ON LIGHT OIL HAIR COMPOSITION

(71) Applicant: Johnson & Johnson Consumer Inc., Skillman, NJ (US)

(72) Inventors: Euen Ekman-Gunn, Skillman, NJ (US); Ana Carolina Nogueira, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/829,214

(22) Filed: Mar. 25, 2020

(65) Prior Publication Data

US 2021/0299027 A1  Sep. 30, 2021

(51) Int. Cl.
| | | |
|---|---|---|
| *A61K 8/891* | (2006.01) | |
| *A61K 8/31* | (2006.01) | |
| *A61K 8/34* | (2006.01) | |
| *A61K 8/36* | (2006.01) | |
| *A61K 8/368* | (2006.01) | |
| *A61K 8/37* | (2006.01) | |
| *A61Q 5/00* | (2006.01) | |
| *A61Q 5/06* | (2006.01) | |
| *A61Q 19/00* | (2006.01) | |

(52) U.S. Cl.
CPC ............. *A61K 8/891* (2013.01); *A61K 8/31* (2013.01); *A61K 8/34* (2013.01); *A61K 8/361* (2013.01); *A61K 8/368* (2013.01); *A61K 8/37* (2013.01); *A61Q 5/002* (2013.01); *A61Q 5/06* (2013.01); *A61Q 19/007* (2013.01)

(58) Field of Classification Search
CPC . A61K 8/891; A61K 8/31; A61K 8/34; A61K 8/361; A61K 8/368; A61K 8/37; A61Q 5/002; A61Q 5/06; A61Q 19/007
See application file for complete search history.

(56) References Cited

U.S. PATENT DOCUMENTS 4,243,657 A * 1/1981 Okumura ............... A61Q 5/00
424/DIG. 1
10,105,292 B2 * 10/2018 Fageon .................... A61K 8/35
(Continued)

FOREIGN PATENT DOCUMENTS

CN 110200850 A 9/2019
CN 110812252 A 2/2020
(Continued)

OTHER PUBLICATIONS

Pharmacentral, Dimethicone Excipient, 2022; screenshots from Wayback Machine: https://pharmacentral.com/product/dimethicone-pharmaceutical-excipient/, PharmaCentral (Year: 2022).*

(Continued)

*Primary Examiner* — Bethany P Barham
*Assistant Examiner* — Ayaan A Alam
(74) *Attorney, Agent, or Firm* — Samuel J. Gee

(57) ABSTRACT

The present disclosure relates to leave-on light oil hair compositions that comprise a blend of non-cyclic silicone and non-silicone ingredients. The leave-on light oil hair compositions, which do not contain D4, D5 or D6 silicones, are particularly useful in methods for imparting durable resistance to breaking, frizz control, shine and/or volume definition with a soft feel to hair.

14 Claims, 24 Drawing Sheets

(56) References Cited

U.S. PATENT DOCUMENTS

| | | | |
|---|---|---|---|
| 10,555,893 | B2 | 2/2020 | Parikh et al. |
| 10,561,596 | B2 | 2/2020 | Simonnet et al. |
| 2010/0047296 | A1 | 2/2010 | Banowski et al. |
| 2013/0272975 | A1 | 10/2013 | Nguyen |
| 2013/0272979 | A1* | 10/2013 | Nguyen ............... A61K 8/585 424/60 |
| 2014/0370062 | A1 | 12/2014 | Fageon |
| 2015/0296953 | A1 | 10/2015 | Murdock et al. |
| 2015/0297485 | A1 | 10/2015 | Kleinen et al. |
| 2018/0104210 | A1 | 4/2018 | Abdel-Rahman |
| 2018/0214361 | A1* | 8/2018 | Kojoma ............... A61K 8/31 |
| 2018/0289605 | A1 | 10/2018 | Punyani |
| 2018/0303744 | A1 | 10/2018 | Dörr et al. |
| 2019/0076341 | A1 | 3/2019 | Lipinski |
| 2019/0083375 | A1 | 3/2019 | Gough |
| 2019/0099340 | A1* | 4/2019 | Fields ............... A61K 8/24 |
| 2020/0188253 | A1* | 6/2020 | Krohn ............... A61Q 5/12 |
| 2020/0253856 | A1 | 8/2020 | Kryzsik |

FOREIGN PATENT DOCUMENTS

| | | | |
|---|---|---|---|
| CN | 110876697 | A | 3/2020 |
| DE | 102011087975 | A1 | 6/2013 |
| EP | 1815841 | | 8/2007 |
| EP | 2392314 | A1 | 12/2011 |
| JP | 2008056640 | A | 3/2008 |
| JP | 2017193499 | A | 10/2017 |
| JP | 2019178108 | A | 10/2019 |
| RU | 2004120294 | A | 3/2005 |
| WO | WO 2011/086073 | | 7/2011 |
| WO | WO-2016175524 | A1 * | 11/2016 ............... A61K 8/34 |
| WO | WO 2018/098542 | A1 | 6/2018 |
| WO | WO 2019/060088 | A1 | 3/2019 |
| WO | WO 2019060089 | A1 | 3/2019 |

OTHER PUBLICATIONS

IMAP, Trisiloxane, octamethyl-: Human health tier II assessment, 2018, Accelerated Assessment of Industrial Chemicals in Australia; from https://www.industrialchemicals.gov.au/sites/default/files/Trisiloxane%2C%20octamethyl-_Human%20health%20tier%20II%20assessment.pdf (Year: 2018).*

The Cosmetic Chemist, Dimethicone, 2022; from http://www.thecosmeticchemist.com/molecule_of_the_week/dimethicone.html (Year: 2022).*

Machine translation of WO-2016175524-A1 from FIT via PE2E, 2016 (Year: 2016).*

Database GNPD [Online] Mintel; Oct. 8, 2019, "Argan Oil Styling", XP055814356, Database accession No. 6917741 "the whole document".

Database GNPD [Online] Mintel; Oct. 10, 2017, "Weightless Oil Mist", XP055814359, Database accession No. 5156995 "the whole document".

Database GNPD [Online] Mintel; Mar. 9, 2010, "Mellow Split Ends Repairing Sealing Serum", XP055814362, Database accession No. 1289419 "the whole document".

PCT International Search Report for PCT/IB2021/052391, dated Jun. 17, 2021.

Smooth Closer: The latest in silicones and silicone alternatives, Sep. 4, 2019, https://www.cosmeticsbusiness.com/news/article_page/Smooth_closer_The_latest_in_silicones_and_silicone_alternatives/157719.

(Lefaudeux et al., Third Annual Conference on Applied Hair Science, Sep. 2008, http://www.spequation.com/files/journalof-cosmetic-science-bossa-nova-tech-60-153-169-march-april-2009_5b45fb50b1be0.pdf) pp. 1-16.

Hongjiu, Organic Silicone Production and Application Technology; Institute of Scientific and Technological Information, Ministry of Chemical Industry; Dec. 31, 1985; pp. 261-262.

Silicones on the spot—again // Jan. 20, 2020, URL: https://www.obelis.net/news/silicones-on-the-spot-again/, found on Jul. 30, 2024.

Sutyagin V.M. et al., "Chemistry and Physics of Polymers: Textbook" [in Russian], Tomsk: TPU Publishing House, 2003, (see p. 142 para. 1-2 from the bottom, p. 132 para. 4-5 from the bottom, p. 140 para. 2 from the bottom, p. 151 para 1 from the bottom, p. 173 para. 2 from the top).

Database GNPD [Online] Mintel; Feb. 6, 2020, "I Love My Sleek 5 in 1 My Smoothing Spray-On Serum" XP055814659, Database accession No. 7245231 "the whole document".

PCT International Search Report for PCT/IB2021/052395, Dated Jun. 17, 2021.

PCT International Search Report for PCT/IB2021/052397, Dated Jun. 17, 2021.

* cited by examiner

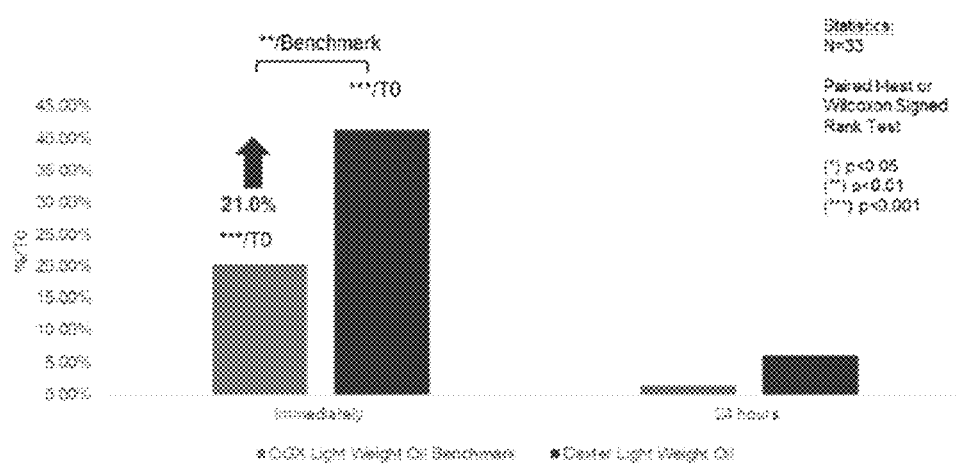
Fig. 2 – Scalp Moisturization Evaluated with DermaLab

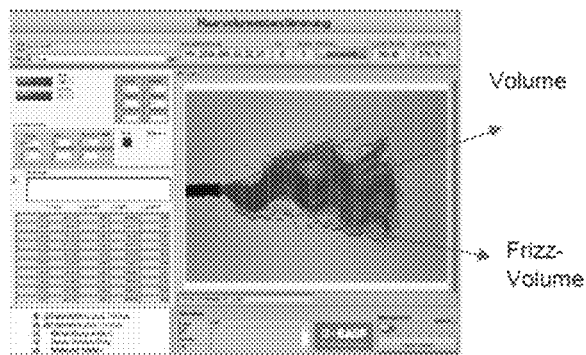
Fig. 3 - Volume / Frizz – Volume Imaging

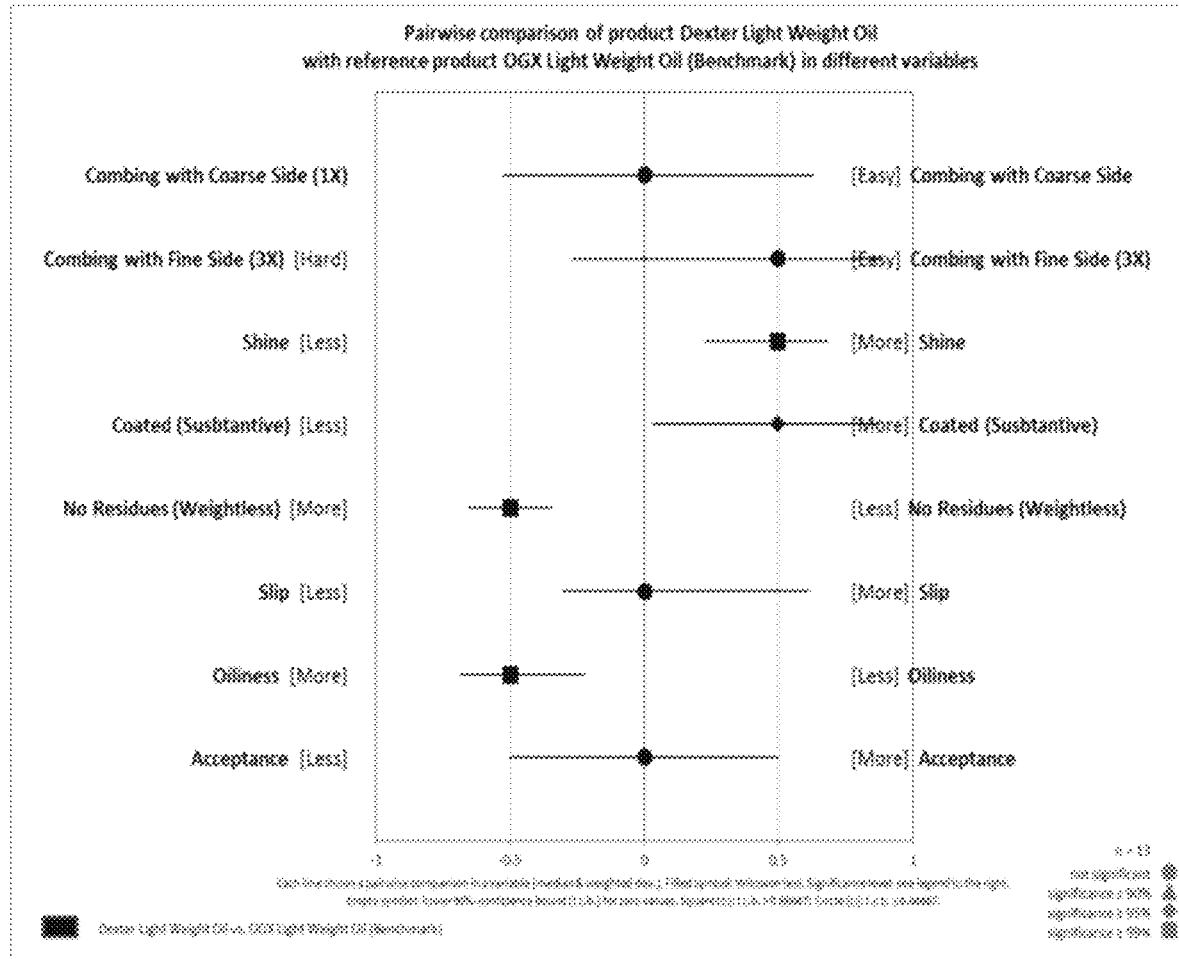
Fig. 5a. Wet Sensory Assessment on Medium Bleached Caucasian Hair

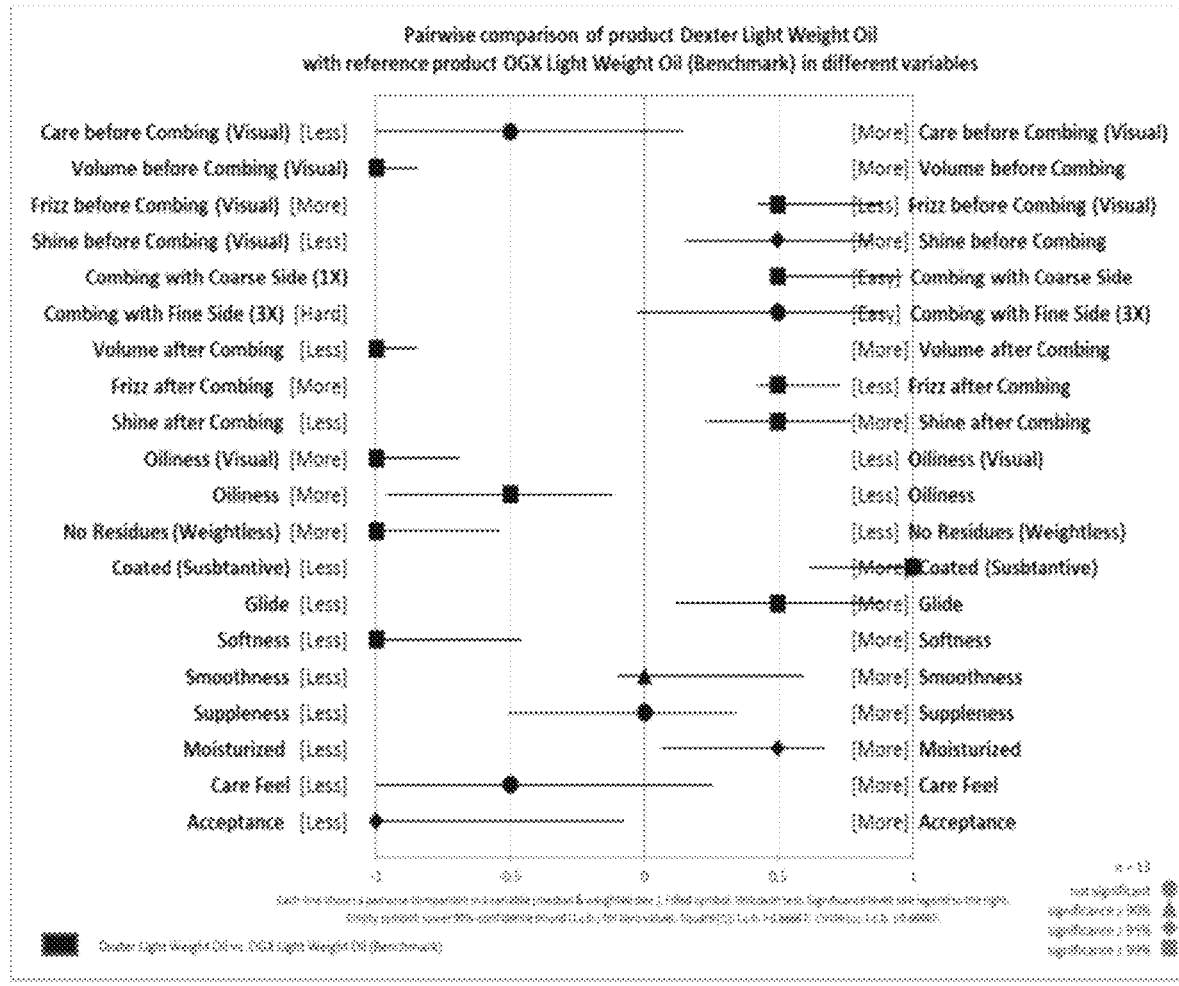
Fig. 5b. Dry Sensory Assessment on Medium Bleached Caucasian Hair

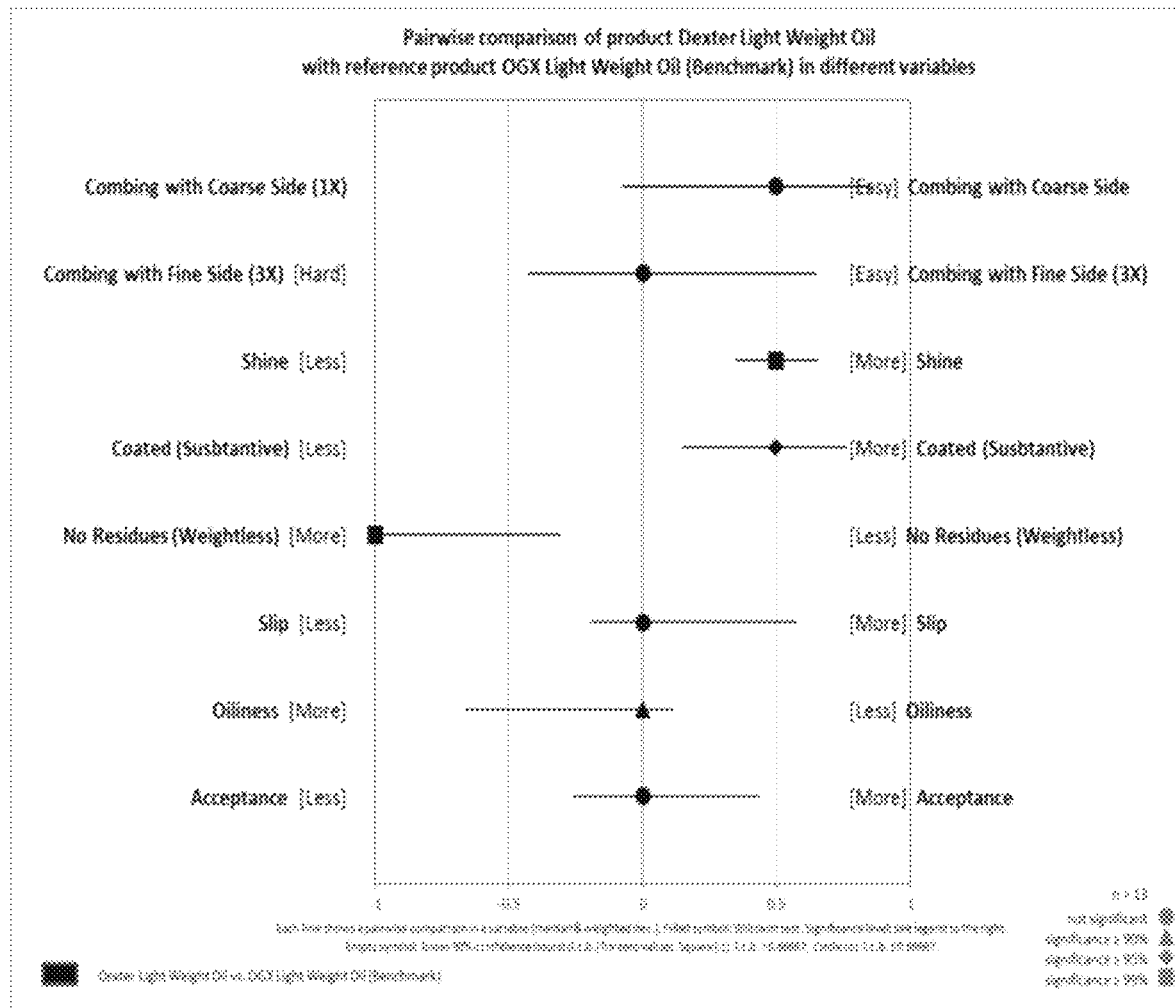
Fig. 6a. Wet Sensory Assessment on Brazilian Curly Hair

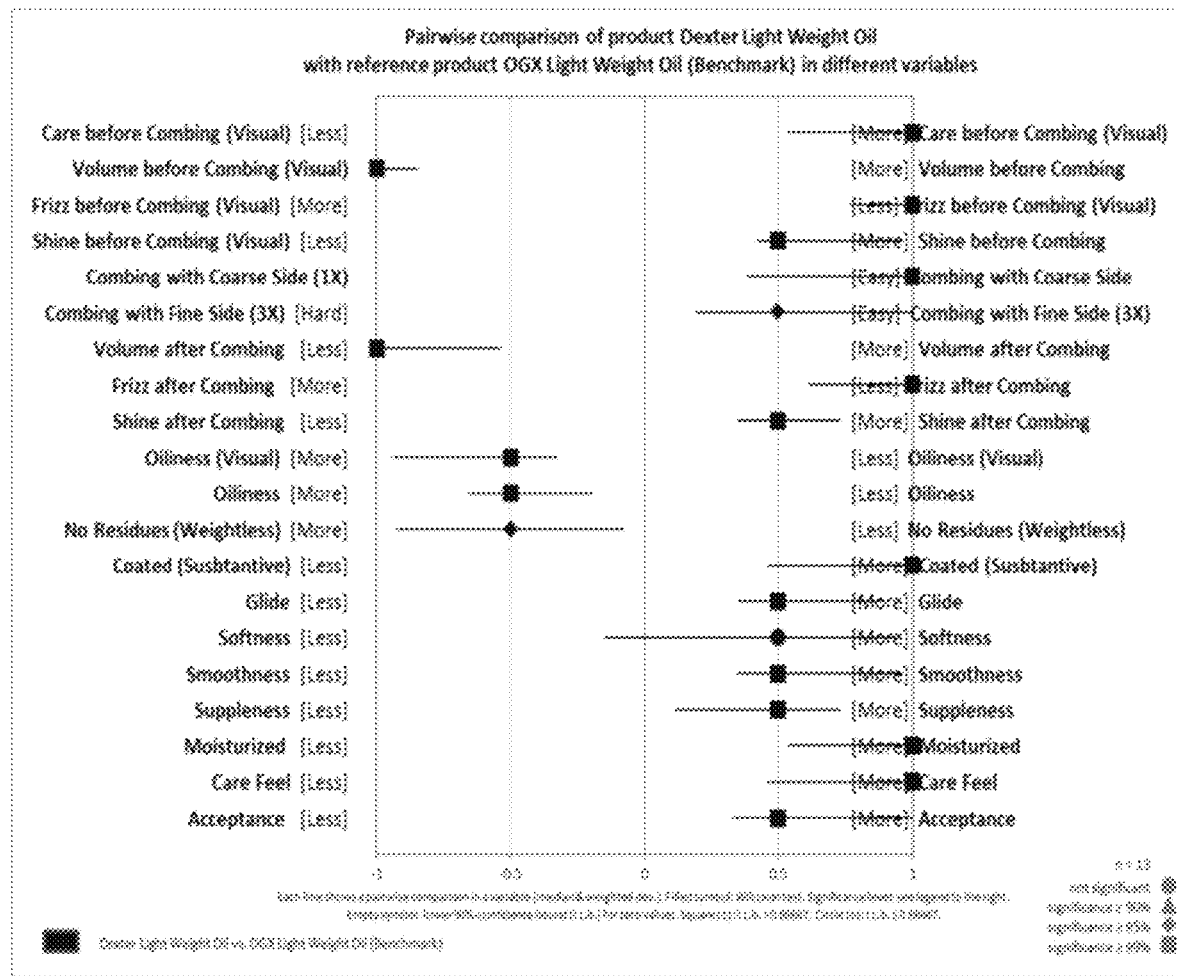
Fig. 6b. Dry Sensory Assessment on Brazilian Curly Hair

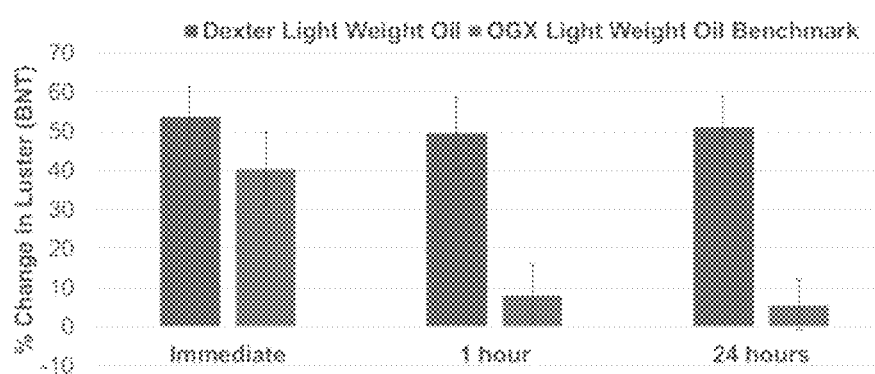
Fig. 7. Luster Comparison between the oils at different time points

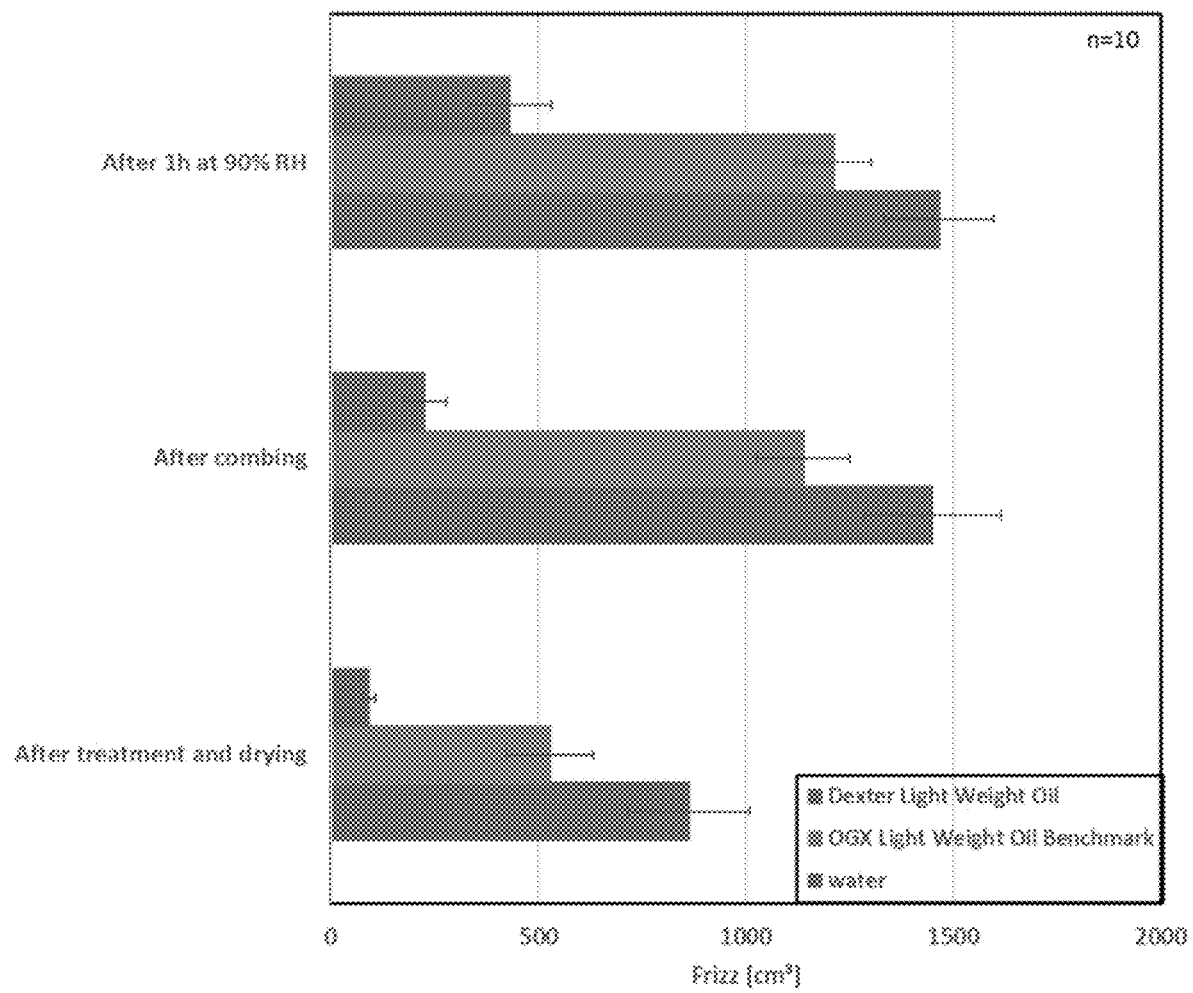
Fig. 9. Frizz Volume comparison between the oils at different treatment conditions

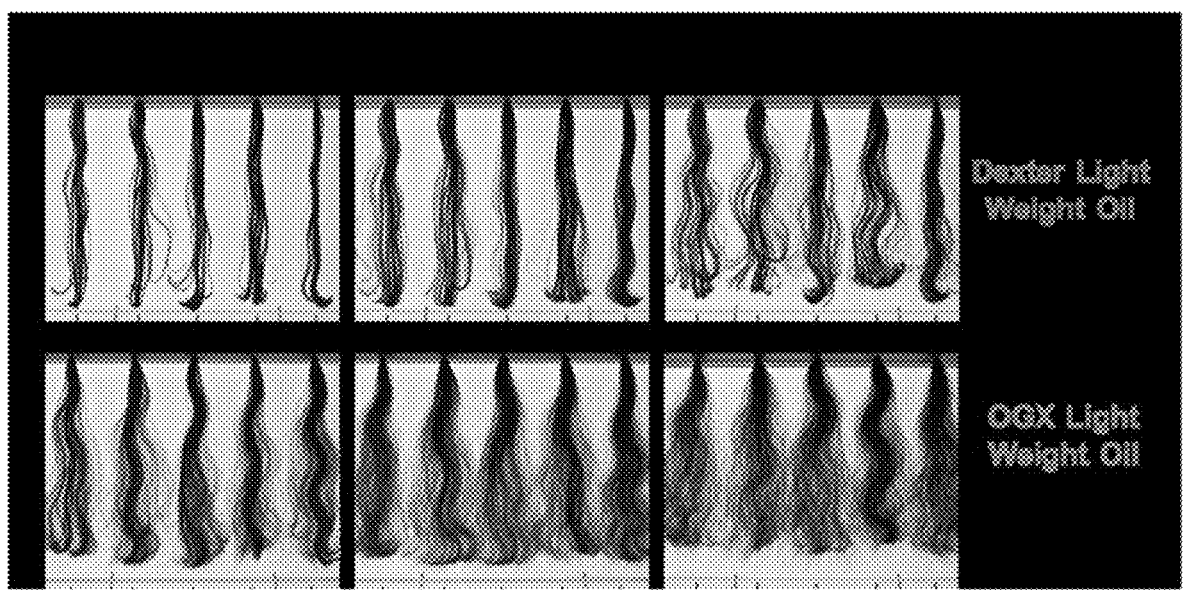
Fig. 10. Visual comparison of hair tresses between the oil treatments

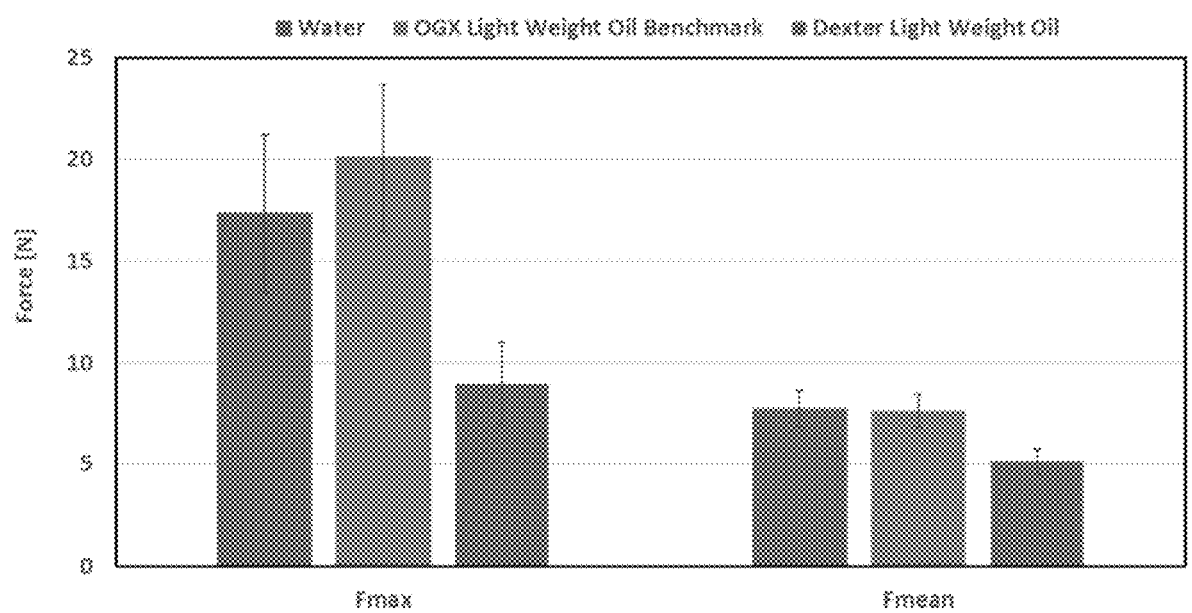
Fig. 11. Force comparison to pull hair tress between oil treatments

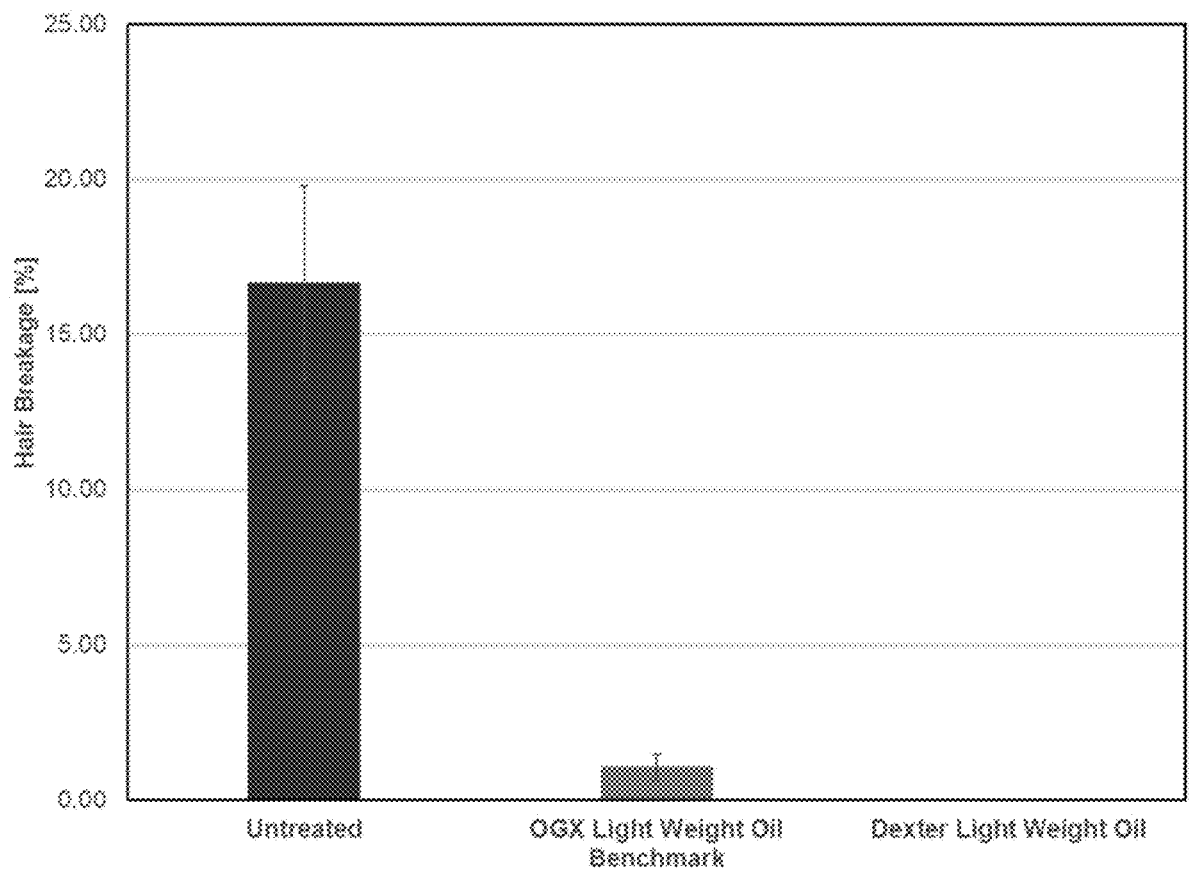
Fig. 12. Hair breakage [%] comparison between oil treatments

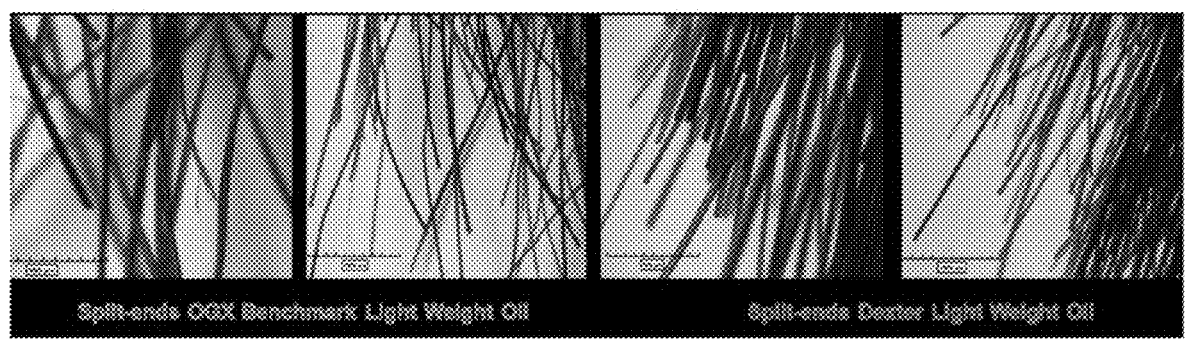
Fig. 13. Split-ends comparison between oil treatments at different magnifications Weight Loss is represented by grams of hair loss from a 2 gram tress.

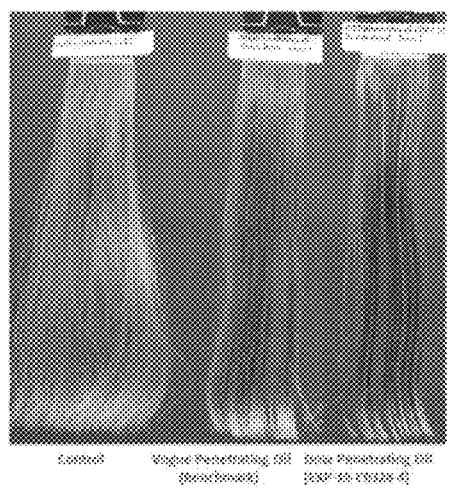 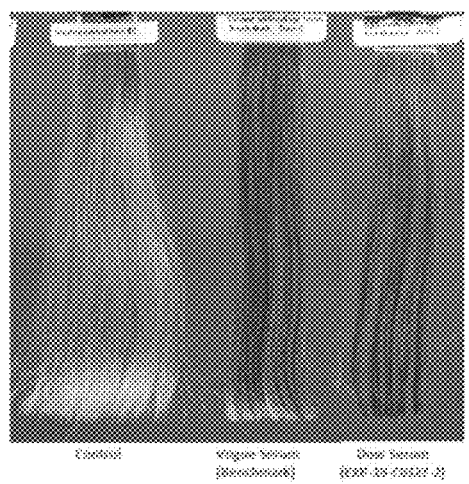
Fig. 20a                    Fig. 20b

LEAVE-ON LIGHT OIL HAIR COMPOSITION

FIELD OF THE INVENTION

The present disclosure relates to compositions for treating or styling hair.

BACKGROUND OF THE INVENTION

Silicones, which are a class of polymers with a chemical structure based on chains of alternate silicon and oxygen atoms, with organic groups attached to the silicon atoms, have been useful and versatile cosmetic ingredients. They range in viscosity from volatile liquids to solid pastes and have been used as emollients that provide unique sensorial properties, hair conditioning agents, emulsifiers and for the surface treatment of pigments. Siloxanes are functional groups that have a molecular structure based on a chain of alternate silicon and oxygen atoms, especially (as in silicone) with organic groups attached to the silicon atoms. Cyclic siloxanes (cyclosiloxanes) are basic members of the broad family of silicone materials. All silicone materials share common chemistry but each substance is different when it comes to its properties and use.

Among the large family of siloxanes, cyclomethicone is a generic name for a cyclic siloxane with a general formulation of $(CH_3)_{2n}O_nSi_n$, where n=3-7. Examples include D4 (n=4, INCI: cyclotetrasiloxane); D5 (n=5, INCI: cyclopentasiloxane); and D6 (n=6; INCI: cyclohexasiloxane).

A common denominator for cyclosiloxanes is that they contain repeating units of silicone (Si) and oxygen (O) atoms in a closed loop, giving it a "cyclic" structure.

This also gives cyclosiloxanes their unique properties as hybrid inorganic-organic substances. D4, D5 and D6, which contain 4, 5 and 6 repeating units respectively, (see FIGS. 1a-1c), are the three main cyclosiloxanes used in commercial production.

D4, D5 and D6 are each odorless, colorless liquids that are mostly used as an intermediate or basic raw material in the production of silicone rubbers, gels and resins. When used as an intermediate during the manufacturing process, virtually all of D4, D5 and D6 are consumed with only a tiny amount remaining in final products.

Generally, siloxanes are well tolerated by human organisms. However, the degree of polymerization, format of the polymer (linear or cyclic), and molecular weight can affect the toxicity of this group of chemicals.

These ingredients have wide applications in cosmetic products such as emollient, humectant, solvent, viscosity control and hair conditioning.

However, concerns have been raised about their toxicity and effects on the environment.

In an assessment published in 2016 (SCCS/1549/15), the Scientific Committee on Consumer Safety (SCCS), an independent scientific committee that provides the European Commission with scientific advice, recommended that impurities of D4 and D5 should be kept as low as possible.

It is now required that the concentration of D4, D5 and D6 in some cosmetic products placed on the European market be less than 0.1% by weight.

U.S. Published Application No. 20180303744 to Covestro Deutschland AG discloses the use of a cosmetic composition that comprises a water-dispersible polyurethane for the treatment of human hair.

U.S. Published Application No. 20150297485 to Evonik Industries AG discloses a composition that comprises at least one esterification product of at least one polyhydric alcohol and at least one fatty acid. The reference discloses that the composition, which is readily foaming and structured, has a high oil fraction.

IN295649B to BASF SE discloses cosmetic formulations that comprise copolymers comprising N-vinylpyrrolidone and a hydrophobically modified acrylic acid derivative U.S. Published Application No. 20100047296 to Henkel AG & Co. KGaA discloses an oil-in-water dispersion/emulsion cosmetic or dermatological stick compositions.

U.S. Pat. No. 10,555,893 to L'Oreal discloses a leave-on hair styling composition that comprises beeswax; glucoside emulsifiers; ester oils and/or emulsifying esters; water; monomeric polyols; and one or more fatty acids and/or fatty alcohols.

Smooth closer: The latest in silicones and silicone alternatives, Sep. 4, 2019, https://www.cosmeticsbusiness.com/news/article_page/Smooth_closer_The_latest_in_silicones_and_silicone_alternatives/157719, discloses silicones and silicone alternatives for use in personal care. The reference discloses that BASF's Cetiol C5 (INCI: Coco caprylate), Cetiol CC (INCI: Dicapryl carbonate) and Cetiol Ultimate (INCI: Undecane, tridecane), are potential emollients that can be used. The reference also discloses that dimethicone can be used.

A need exists for alternatives to D4, D5 and D6 that are of low cost; stable at room temperature; and that provide good performance.

SUMMARY OF THE INVENTION

It is an object of the invention to provide a leave-on hair composition that moisturizes the hair and scalp.

It is another object of the invention to provide a leave-on hair composition the prevents damage from surfactants such as sodium lauryl sulfate that are in most shampoos.

It is a further object of the invention to provide a leave-on hair composition that promotes a healthy scalp in between shampooing.

It is yet a further object of the invention to provide a leave-on hair composition that moisturizes the hair and scalp.

It is a further object of the invention to provide a leave-on hair composition that promotes properties such as, but not limited to, frizz control; breakage resistance; shine; volume; reduced split ends; and curl definition.

To accomplish the above and related objects, the invention is embodied in the accompanying description. Variations are contemplated as being part of the invention, limited only by the scope of the claims.

The invention is a hair composition that is useful for nourishing hair that comprises a blend of non-cyclic silicone and non-silicone ingredients. The hair composition delivers the benefit of making hair smooth and manageable while not too sticky when applied as a leave-on. The composition, which is free of cyclic silicones such as D4, D5 and D6 silicones, exhibits superior benefits to hair compared to hair compositions having volatile silicones.

BRIEF DESCRIPTION OF THE DRAWINGS

FIG. 2 is a graph showing scalp moisturization evaluated with DermaLab.

FIG. 3 is an image showing volume/frizz-volume imaging.

FIG. 5a is a graph showing wet sensory assessment on medium bleached caucasian hair.

FIG. 5b is a graph showing dry sensory assessment on medium bleached caucasian hair.

FIG. 6a is a graph showing wet sensory assessment on Brazilian curly hair.

FIG. 6b is a graph showing dry sensory assessment on Brazilian curly hair.

FIG. 7 is a graph showing the percentage change in luster comparing Light Oil composition of the invention and Light Oil Benchmark at different time points.

FIG. 9 is a graph showing frizz volume comparison between Light Oil composition of the invention and Light Oil Benchmark at different treatment conditions.

FIG. 10 is a photograph showing comparison of hair tresses between Light Oil composition of the invention and Light Oil Benchmark.

FIG. 11 is a graph showing Fmax (Maximum Force) and Fmean (Mean Force) to pull hair tresses through Zwick comparison between Light Oil composition of the invention and Light Oil Benchmark.

FIG. 12 is a graph showing comparison hair breakage [%] between Light Oil composition of the invention and Light Oil Benchmark.

FIG. 13 are images showing split-ends of hair treated with Light Oil composition of the invention and with Light Oil Benchmark at different magnifications.

FIG. 20a and FIG. 20b are images showing volume down for Penetrating Oil Benchmark, Penetrating Oil composition of the invention, Serum Benchmark and Serum composition of the invention.

DETAILED DESCRIPTION OF THE INVENTION

Figure 1A:
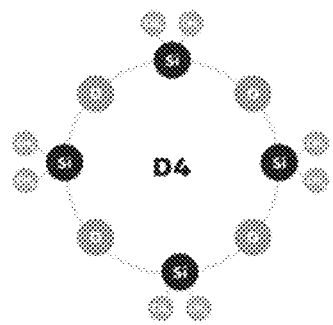
FIGS. 1a-1c show the chemical structure of D4 (FIG. 1a), D5 (FIG. 1b) and D6 (FIG. 1c), respectively.
Figure 1B:
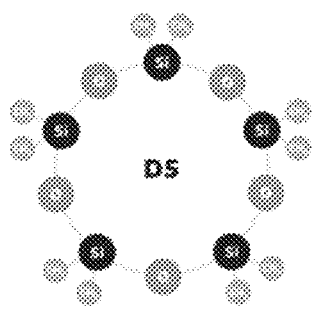
Figure 1C:
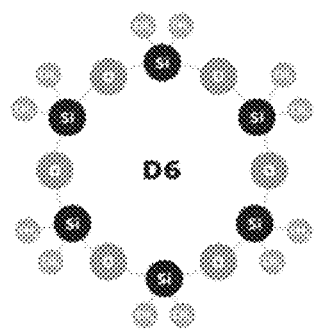

The ability of non-cyclic silicone and non-silicone oils to meet or outperform D4, D5 and/or D6 in hair care compositions were assessed.

Definitions

Products

In terms of benefits to the hair, the leave-on hair compositions of the invention are similar (i.e., all give shine, moisturization, etc.); the main difference among the product formats listed below is the viscosity and application process.

Hair Oils

Hair oils lubricate the hair and can penetrate the cuticles, causing changes to the hair structure by adding fatty acids to replace the lipids in hair. Hair oils can be applied at various stages of the hair care process, including during blow drying or diffusing, as an overnight treatment and even before washing as a rinse-out treatment.

Light Oil is thinner and generally used in a sprayable bottle. Light Oils have little to no hair penetration.
  Penetrating Oil is more viscous than light oil and generally not sprayable. Penetrating Oils have high penetration.

Hair Serum

Hair serums generally work best when they are applied to wet hair. Serums work by sealing the cuticles and fusing with hair strands to create a lasting protective layer.

Serum is more viscous than light oil and not sprayable. Serums, which sit on the outside of the cuticle, generally don't penetrate hair.

The viscosities affect consumer perception and to achieve this necessarily a different combination of ingredients is needed for each product format.

Ingredients

The ingredients below that contain silicon (Si) are non-cyclic silicone ingredients and the ingredients below that do not contain silicon are non-silicone ingredients.

$C_{12-15}$ alkyl benzoate is an ester of a mixture of $C_{12}$ to $C_{15}$ primary and branched alcohols and benzoic acid.

Coco-caprylate caprate is the caprylic/capric acid ester of saturated fatty alcohol $C_{12-18}$.

Dimethicone is a linear silicone polymer having the molecular formula $C_8H_{24}O_2Si_3$.

Isododecene is an acyclic alkane having the molecular formula $C_{12}H_{26}$.

Isopropyl myristate is the ester of isopropyl alcohol and myristic acid having the molecular formula $C_{17}H_{34}O_2$.

Octyldodecanol is a long chain fatty alcohol having the molecular formula $C_{20}H_{42}O$.

Propylheptyl caprylate is a linear alkyl ester having the molecular formula $C_{18}H_{36}O_2$.

Additional non-cyclic silicone ingredients that may be employed and their properties are disclosed in U.S. Pat. No. 10,105,292 to L'Oreal, the entire contents of which are incorporated by reference herein. The reference discloses that these ingredients have the following properties:

A molecular weight between 500 and 100,000 g/mol; a viscosity at 25° C. ranging from 4 to 5000 mm²/s, more preferred from 4 to 1000 mm²/s and even more preferred from 4 to 200 mm²/s. The reference discloses that the "kinematic viscosity at 25° C. raw product CID-012-01" or the "Ubbelohde viscosity at 25° C. DIN 51562-1 PVO4001" method may be employed to measure molecular weight.

A refractive index of greater than 1.3 and especially less than 1.6.

The general formula (I) below:

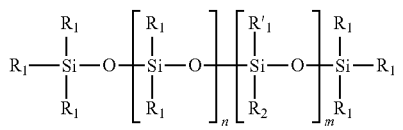

with: $R_1$, which may be identical or different, representing: i) a linear or branched ($C_1$-$C_{20}$) alkyl group, particularly a linear or branched $C_1$-$C_6$ group, such as methyl, ethyl, propyl or butyl; or ii) a hydroxyl group; $R_2$ representing: i) a linear or branched ($C_1$-$C_{20}$) alkyl group optionally interrupted and/or terminated with a heteroatom such as 0, S or N; in particular, i) is a linear or branched $C_1$-$C_6$ alkyl group, such as methyl, ethyl, propyl or butyl; ii) a group ($C_1$-$C_9$)(poly)haloalkyl, especially perfluoroalkyl, comprising from 1 to 9 halogen atoms, particularly fluorine, such as trifluoromethyl; and iii) the polysiloxane group —O—[Si($R_1$)$_2$—O]n'—Si($R_1$)$_3$ with $R_1$ as defined previously; $R'_1$ representing a radical $R_1$ or $R_2$ as defined previously; m being an integer inclusively between 0 and 150 and preferably between 20 and 100; n and n', which may be identical or different, being an integer inclusively between 1 and 300 and preferably between 1 and 100.

Preferably, the non-cyclic silicone ingredient(s) in accordance with the invention is(are) present in a content ranging from about 10% to about 98% by weight relative to the total weight of the composition.

Preferably, the non-cyclic silicone ingredient(s) in accordance with the invention is(are) present in a leave-on light oil hair composition in a content ranging from about 10% to about 25%, more preferably about 12%, by weight relative to the total weight of the leave-on light oil hair composition.

Preferably, the non-cyclic silicone ingredient(s) in accordance with the invention is(are) present in a leave-on penetrating oil hair composition in a content ranging from about 30% to about 80%, more preferably about 75%, by weight relative to the total weight of the leave-on penetrating oil hair composition.

Preferably, the non-cyclic silicone ingredient(s) in accordance with the invention is(are) present in a leave-on serum hair composition in a content ranging from about 85% to about 99.5%, more preferably about 95%, by weight relative to the total weight of the leave-on penetrating oil hair composition.

Additional non-silicone ingredients that may be employed and their properties are disclosed in U.S. Pat. No. 10,105, 292 to L'Oreal, the entire contents of which are incorporated by reference herein. The reference discloses that these ingredients:

May be made of hydrocarbon-based oils of plant origin such as triglyceride esters, which are generally fatty acid triesters of glycerol, the fatty acids of which may have chain lengths varying from $C_4$ to $C_{24}$, wherein the chains may be linear or branched, and saturated or unsaturated; wherein the oils include wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil and musk rose oil; or caprylic/capric acid triglycerides, for example those sold by the company Stearineries Dubois or those sold under the names Miglyol 810, 812 and 818 by the company Dynamit Nobel, (ii) synthetic ethers containing from 10 to 40 carbon atoms; (iii) linear or branched hydrocarbons of mineral or synthetic origin, such as petroleum jelly, polydecenes, hydrogenated polyisobutene such as Parleam, and squalane, and mixtures thereof; (iv) synthetic esters, for example the oils of formula RCOOR' in which R represents a linear or branched fatty acid residue comprising from 1 to 40 carbon atoms and R' represents a hydrocarbon-based chain that is especially branched, containing from 1 to 40 carbon atoms, on condition that R+R'≥10, for example purcellin oil (cetostearyl octanoate), isopropyl myristate, isopropyl palmitate, $C_{12}$-$C_{15}$ alkyl benzoate, for example the product sold under the trade name Finsolv TN or Witconol TN by the company Witco or Tegosoft TN by the company Evonik Goldschmidt, 2-ethyl phenyl benzoate, for example the commercial product sold under the name X-Tend 226 by the company ISP, isopropyl lanolate, hexyl laurate, diisopropyl adipate, isononyl isononanoate, oleyl erucate, 2-ethylhexyl palmitate, isostearyl isostearate, alcohol or polyalcohol octanoates, decanoates or ricinoleates, for example propylene glycol dioctanoate; hydroxylated esters, for example isostearyl lactate, diisostearyl malate; and pentaerythritol esters; citrates or tartrates, for example linear $C_{12}$-$C_{13}$ dialkyl tartrates, such as those sold under the name Cosmacol ETI by the company Enichem Augusta Industriale, and also linear $C_{14}$-$C_{15}$ dialkyl tartrates such as those sold under the name Cosmacol ETL by the same company; acetates; (v) fatty alcohols that are liquid at room temperature, containing a branched and/or unsaturated carbon-based chain containing from 12 to 26 carbon atoms, for example octyldodecanol, isostearyl alcohol, oleyl alcohol, 2-hexyldecanol, 2-butyloctanol or 2-undecylpentadecanol; (vi) higher fatty acids such as oleic acid, linoleic acid or linolenic acid; (vii) carbonates such as dicaprylyl carbonate, for example the product sold under the name Cetiol CC by the company Cognis; (viii) fatty amides, for example isopropyl N-lauroyl sarcosinate, for example the product sold under the trade name Eldew SL205 from Ajinomoto; and mixtures thereof.

Preferably, the non-silicone ingredient(s) in accordance with the invention are present in a content ranging from about 2% to about 90% by weight relative to the total weight of the composition.

Preferably, the non-silicone ingredients in accordance with the invention are present in a leave-on light oil hair composition in a content ranging from about 75% to about 90%, more preferably about 88%, by weight relative to the total weight of the composition.

Preferably, the non-silicone ingredients in accordance with the invention are present in a leave-on penetrating oil hair composition in a content ranging from about 20% to about 70%, more preferably about 25%, by weight relative to the total weight of the composition.

Preferably, the non-silicone ingredients in accordance with the invention are present in a leave-on serum hair composition in a content ranging from about 0.5% to about 15%, more preferably about 5%, by weight relative to the total weight of the composition.

Technical Terms

Kinematic viscosity is a measure of a fluid's internal resistance to flow under gravitational forces.

Tensile strength is the ability of a material to resist breaking/tearing.

A tensile test applies tensile (pulling) force to a material and measures the specimen's response to the stress. By doing this, tensile tests determine how strong a material is and how much it can elongate.

An Ubbelohde type viscometer or suspended-level viscometer is a measuring instrument which uses a capillary based method of measuring viscosity. The advantage of this instrument is that the values obtained are independent of the total volume.

Statistical Methods

Paired Student t test consist of a sample of matched pairs of similar units, or one group of units that has been tested twice.

Shapiro-Wilk Test is a test of normality in frequentist statistics. Normality tests are used to determine if a data set is well-modeled by a normal distribution and to compute how likely it is for a random variable underlying the data set to be normally distributed.

Turkey's Test is a single-step multiple comparison procedure and statistical test. It can be used to find means that are significantly different from each other.

Wilcoxon Signed Rank Test is a non-parametric statistical hypothesis test used to compare two related samples, matched samples, or repeated measurements on a single sample to assess whether their population mean ranks differ.

EXAMPLES

Leave-on hair compositions free of the direct addition of cyclic silicones such as cyclotetrasiloxane (D4), cyclopentasiloxane (D5) and cyclohexasiloxane (D6) have been developed. The compositions meet consumer expectations for aesthetics; are cost effective; and meet global compliance requirements.

The following product formats were assessed:
1) Light Oil
2) Penetrating Oil
3) Serum Prototypes of each product format with acceptable appearance parity to the respective benchmarks were further evaluated in accordance with below:

1-week stability at 5° C. and 60° C. at room temperature (RT);

Appearance (physical conditions, for example, color, odor, shape) at 24 hours (h) and at 1-week;

Lubrication (measured by wet and dry combing in in-vitro—tresses test); and

Cost.

Final prototypes were selected and the following tests were conducted:

Stability according to the requirements below:
3 months at 5° C.±3° C.: used as Control for comparison of appearance (physical conditions, for example, color, odor, shape);
3 months at 25° C.±2° C./60% f 5% RH (physical conditions, initial and 3 months);
3 months and 6 months at 40° C.±2° C./75%±5% RH (physical conditions at 1, 3 and 6 months);
1 month at 50° C. (physical conditions at 1 month).

In-vitro Tests

Frizz Control (Caucasian and textured hair) at high humidity
Deliverable: Pictures at 0 h, 4 h, 8 h, and 24 h Combing (wet and dry)
Deliverable: graphs showing % reduction in total work before and after treatment Resist breakage caused by brushing and styling (anti-breakage test)
Deliverable: graphs showing % reduction in total breakage before and after treatment Shine
Deliverable: Panel testing or Samba measurements Volume (image analysis)
Deliverable: Image analysis results and panel testing Improved split-ends (SEM)
Deliverable: SEM images Table 1 shows some properties imparted to hair that were assessed.

TABLE 1

| Test | Conditions | Deliverables |
|---|---|---|
| 1. Frizz Control (caucasian, textured hair) | Frizz control on caucasian, textured hair-conducted at room temperature (RT) and high humidity (80%). (3 samples/test) | Pictures at 0 h, 4 h, 8 h, and 24 h |
| 2. Combing (dry***) | Dry combing only. | Data/graphs showing % reduction in total work before and after treatment |
| 3. Resist breakage caused by brushing and styling (antibreakage test) | Caucasion straight hair, 10,000 cycles | Picture and graphs showing % reduction in total breakage before and after treatment |
| 4. Shine | SAMBA measurements | SAMBA measurements (SAMBA Hair System, Bona Nova Vision, Los Angeles, CA) |
| 5. Volume | Pictures to confirm volume down effect. Hair type caucasian, straight slightly bleached | Pictures at 0 h, 4 h, 8 h, and 24 h |
| 6. Improved splits-ends (to be tested after anti-breakage) | SEM images after resistance to breakage study complete. | Images comparing split ends of the various formulations. |
| 7. Moisturization of positional hair (deposition) | Dry friction test to measure smoothness or water droplet test to show hydrophobicity. | Data or pictures showing reduction of coefficient of friction CoF results |

The following tests were conducted to test a Light Oil composition of the invention formula against a Light Oil Benchmark and a control (hair without treatment) (Control).
1) Moisturization—Evaluated by sensory trained panel.
2) Shine—Assessed using SAMBA.
3) Softness—Evaluated by sensory trained panel.
4) Anti-breakage/strength the hair/split ends—Evaluated using repeated combing and split end quantification. Visualized split end repair using HiRox 3D Digital Microscope, HiRox, Hackensack, NJ.
5) Weightless—Evaluated by sensory trained panel (no residues evaluation).
6) Anti-frizz/curl definition—Evaluated in humidity chamber. Brazilian curly hair assessed to visualize frizz volume/curl definition.
7) Volume—Evaluated with images before and after as part of sensory evaluation.

Below is a summary of all results of the tests with Light Oil composition of the invention.

Has superior sensory performance in comparison to Light Oil Benchmark in providing good substantivity and moisturization on both bleached hair and Brazilian curly hair. Additionally, provides significantly more smoothness and strongly preferred on Brazilian curly hair.

Provided significantly longer-lasting shine over Light Oil Benchmark.

Exhibited excellent anti-frizz benefits when compared to Light Oil Benchmark and holds significantly better definition of the curls even after exposure to high humidity.

Imparted significantly better smoothness/suppleness over Light Oil Benchmark which agrees with sensory evaluation.

Provided significantly lower hair breakage and less split-ends when compared to Light Oil Benchmark.

Relative to the Control, Light Oil composition of the invention showed 41.3% ($p<0.05$) significant improvement in scalp moisturization after 5 minutes (immediate) application. Compared to the Light Oil Benchmark, Light Oil composition of the invention showed 21.0% ($p<0.05$) significantly more improvement in scalp moisturization after 5 minutes (immediate) application.

In summary, Light Oil composition of the invention demonstrated better improvement in scalp moisturization efficacy than that of Light Oil Benchmark.

Example Details Light Oil Composition of the Invention Scalp Moisturization

A study was conducted to evaluate the efficacy of Light Oil composition of the invention on scalp moisturization against Light Oil Benchmark, 5 minutes (immediately) and 24 hours after product application. It was a hemi-scalp, double-blind, and randomized study with 33 female volunteers aged 18-65 years old. Scalp moisturization was measured using the DermaLab Skinlabs 8-pin hydration probe.

Relative to the control, Light Oil composition of the invention treatment showed 41.3% ($p<0.05$) significant improvement in scalp moisturization after 5 minutes (immediate) application.

Compared to Light Oil Benchmark, Light Oil composition of the invention showed 21.0% ($p<0.05$) significantly more improvement in scalp moisturization after 5 minutes (immediate) application.

In summary, Light Oil composition of the invention demonstrated better improvement in scalp moisturization efficacy than that of Light Oil Benchmark.

Materials and Methods

A randomized, double-blind study was conducted on the left and right sides of the scalp.

Subjects Must:
1. Be female, aged 18-65 years.
2. Consider themselves generally in good health.
3. Consider themselves to have a dry and itchy scalp.
4. Understand the test procedures and agree to adhere to all study requirements.
5. Be willing to sign a study Informed Consent.
6. Be willing to disclose to the Lead Coordinator all of their current medications (both prescription and over the counter). For subjects taking medications that the Lead Coordinator has determined to be acceptable for use during the study, the subject must have been taking the medication on a consistent schedule for at least two months prior to start of the study.
7. Be willing to advise to the Lead Coordinator of any changes in the administration of any prescription or over the counter medications that becomes necessary for any reason during the study. This may result in subject being discontinued from the study.
8. Be willing to abstain from drinking caffeinated beverages, smoking and exercising on the day of the study measurements.
9. Be willing to discontinue use of any anti-dandruff, leave-on conditioners, or scalp treatments starting seven days before their first study visit and continuing for the duration of the study.
10. Be willing to discontinue any chemical treatments on the hair or scalp (i.e., chemical straightening, perm, hair color) starting seven days before their first study visit and continuing through the duration of the study.
11. Be willing to refrain from washing their hair for a 24-hour period, in between the first and second study visits.

Subjects Must Not:
1. Be pregnant or breastfeeding or have intentions of becoming pregnant at any time during the study.
2. Currently be under a physician's care for chronic illness, disease or serious medical conditions.
3. Have known hypersensitivity or allergies to personal care products, especially products that have moisturizing ingredients.
4. Be participating in any other study pertaining to scalp as the target area within the last four (4) weeks prior to the start of the study.
5. Have undergone major surgery or plastic surgery in the study area.

35 subjects participated in the study, with a total of 33 completing the study.

Tested Product

| (1) Light Oil composition of the invention Light Oil Composition of the Invention | | | | |
|---|---|---|---|---|
| Function | Trade Name | INCI Name | Supplier | % Weight |
| Solvent | Cetiol LC | Coco-Caprylate/Caprate | BASF | qs up to 27.5 |
| Skin Conditioning Agent-Emolient | Ritamollient TN; Finsolv TN (Tegosoft TN2) | C12-15 Alkyl Benzoate | RITA/Innospec | 2.50 |
| Skin Conditioning Agent-Emolient | Permethyl 99A; Ritacane ID | Isododecane | RITA | 30.00 |

-continued

(1) Light Oil composition of the invention Light Oil Composition of the Invention

| Function | Trade Name | INCI Name | Supplier | % Weight |
|---|---|---|---|---|
| Fragrance | Fragrance | | | 0.50 |
| Skin Conditioning Agent-Emolient | Xiameter PMX 200 Fluid 2 cSt | Dimethicone | Dow | 5.00 |
| Skin Conditioning Agent-Emolient | Xiameter 200 10 cst | Dimethicone | Dow | 7.50 |
| Skin Conditioning Agent-Occlusive | 76 Coconut Oil #550; RITA Coconut Oil 76 | Cocos Nucifer (Coconut) Oil | RITA | 2.00 |
| Skin Conditioning Agent-Emolient | Cetiol Sensoft | Propylheptyl Caprylate | BASF | 2.00 |
| Skin Conditioning Agent-Emolient | Eutanol G | Octyldodecanol | BASF | 3.00 |
| Skin Conditioning Agent-Emolient | Lexol IPM | Isopropyl Myristate | Inolex | 20.00 |

(2) Light Oil Benchmark

Cyclotetrasiloxane
Cylopentasiloxane
C12-C15 Alkyl Benzoate
Argania Spinosa (Argan) Kernel Oil
Theobroma Cacao (Cocoa) Seed Butter
Cocos Nucifera (Coconut) Oil
Persea Gratissima (Avocado) Oil
Phenyl Trimethicone
Fragrance (Parfum)
Red 17 (Cl 26100)
Yellow 11 (Cl 47000)

Treatment
a. Application Modality
  Panelists arrived at the study center with hair and scalp free of any product.
  Hair was parted to expose approximately 10 cm of scalp on both the left and right side of the scalp.
  Panelists acclimated to the conditions of the testing center for 30 minutes.

After the baseline measurement, tested product was applied. One product was applied to the right site, and the other product was applied to the left, in accordance with the randomization table.

0.25 ml of each product was dispersed evenly over the whole application site. The product was massaged into the site for approximately five seconds.

Panelists were instructed not to wash or wet their hair or scalp, or apply any products to their hair or scalp between the their baseline and 24 hour visit.

b. Study Design
  Double-blind test.
  Randomized.
  Comparative study.
  Evolution of parameters was compared to prior to treatment (To) (Control), and versus Light Oil Benchmark formulation.
  Duration of treatment: 24 hours, with measurements immediately (5 minutes) and 24 hours after application.

Evaluation Methods
DermaLab: SkinLab Hydration Probe
  The DermaLab Skinlab Hydration Probe by Cortex Technology, Hadsund, Denmark, is an 8-pin probe designed to measure moisturization levels on the skin and scalp. The pins of the probe allow the probe to achieve good contact with the skin of the scalp, avoiding the hair and resulting in a more accurate scalp moisture measurement. It uses alternating current to measure the conductance of the skin in microsiemens ($\mu$S). The conductance of the skin is positively correlated to the moisture level.

Statistical Analysis

| | OGX Light Weight Oil Benchmark | | | | | Dexter Light Weight Oil | | | | |
|---|---|---|---|---|---|---|---|---|---|---|
| | T0 | T1 (5 min) | T2 (24 hr) | T1-T0 | T2-T0 | T0 | T1 (5 min) | T2 (24 hr) | T1-T0 | T2-T0 |
| Mean | 48.6 | 58.4 | 49.2 | 9.8 | 0.6 | 46.9 | 66.3 | 49.8 | 19.4 | 2.9 |
| SD | 17.3 | 34.5 | 17.4 | 24.8 | 8.0 | 18.9 | 47.9 | 20.0 | 36.7 | 16.8 |
| SEM | 3.0 | 6.0 | 3.0 | 4.3 | 1.4 | 3.3 | 8.3 | 3.5 | 6.4 | 2.9 |
| % T0 | — | — | — | 20.3% | 1.3% | — | — | — | 41.3% | 6.1% |
| StatisticsD0 | — | 0.000 | 0.654 | — | — | — | 0.000 | 0.468 | — | — |
| Statistics/PI | — | — | — | — | — | — | — | — | 0.008 | 0.443 |

SD = standard deviation
SEM = standard error of the mean
Statistics: Wilcoxon Signed Rank Test
Validation of the normality of the studied parameters: Paired Student t Test
Invalidation of the normality of the studied parameters: Wilcoxon Signed Rank Test Results and Discussion
  Tables 3 and 4 and FIG. 2 show the effect of Light Oil composition of the invention and Light Oil Benchmark on scalp moisturization.
  Compared to the controls, both Light Oil composition of the invention and Light Oil Benchmark showed significant increase in scalp moisturization at 5 minutes (Immediately) after application, with 41.3% (p<0.05) and 20.3% increase, respectively.

Compared to Light Oil Benchmark, Light Oil composition of the invention showed 21.0% ($p<0.05$) more increase in scalp moisturization at 5 minutes (Immediately) after application.

These results indicated a better improvement in scalp moisturization with Light Oil composition of the invention than that of Light Oil Benchmark at 5 minutes (immediately) after application.

Table 2—Scalp Moisturization Evaluated with DermaLab

CONCLUSION

Light Oil composition of the invention and Light Oil Benchmark showed a significant increase in scalp moisturization at 5 minutes (immediately) after product application. Light Oil composition of the invention also showed better improvement in scalp moisturization than that of Light Oil Benchmark.

TABLE 3

Detailed Results of Scalp Moisturization by DermaLab

| | | OGX Light Weight Oil Benchmark | | | Dexter Light Weight Oil | | |
|---|---|---|---|---|---|---|---|
| Study ID | Initials | Baseline (T0) | 5 min (T1) | 24 hr (T2) | Baseline (T0) | 5 min (T1) | 24 hr (T2) |
| 1 | RH | 65.5 | 59.7 | 72.5 | 45.1 | 70.9 | 85.9 |
| 2 | WC | 41.8 | 49.3 | 44.0 | 44.7 | 56.3 | 51.2 |
| 3 | AC | 61.9 | 83.5 | 59.2 | 59.3 | 78.0 | 60.4 |
| 4 | PP | 59.5 | 66.6 | 64.9 | 60.5 | 66.9 | 53.8 |
| 5 | AM | 59.9 | 59.4 | 50.1 | 48.8 | 69.7 | 53.8 |
| 6 | DC | 35.9 | 27.0 | 32.4 | 17.3 | 18.0 | 21.0 |
| 7 | DE | 83.5 | 225.0 | 81.8 | 93.9 | 304.5 | 96.2 |
| 8 | MP | 31.7 | 41.5 | 26.2 | 46.1 | 58.2 | 40.1 |
| 9 | LF | 42.0 | 44.1 | 47.8 | 50.3 | 63.1 | 37.5 |
| 10 | MM | 43.0 | 42.4 | 38.2 | 27.8 | 46.2 | 34.0 |
| 11 | LR | 50.9 | 62.5 | 56.5 | 73.0 | 69.4 | 34.4 |
| 12 | LG | 72.5 | 69.8 | 67.6 | 85.8 | 78.8 | 72.5 |
| 13 | AB | 33.5 | 44.4 | 37.3 | 53.1 | 79.4 | 45.0 |
| 14 | JC | 31.7 | 40.8 | 25.7 | 38.1 | 46.9 | 28.0 |
| 15 | JT | 49.9 | 50.4 | 45.9 | 40.7 | 40.5 | 35.4 |
| 16 | KF | 17.9 | 34.6 | 18.1 | 21.5 | 15.7 | 18.4 |
| 17 | JJ | 33.0 | 32.0 | 27.7 | 20.4 | 49.5 | 25.1 |
| 18 | DM | 60.3 | 58.3 | 54.6 | 47.6 | 63.7 | 84.3 |
| 19 | MH | 45.1 | 63.5 | 29.5 | 51.3 | 73.0 | 47.9 |
| 20 | RD | 90.7 | 101.8 | 83.4 | 77.5 | 97.4 | 55.6 |
| 22 | AM | 34.0 | 55.5 | 51.1 | 27.9 | 45.2 | 39.8 |
| 23 | NS | 56.5 | 52.6 | 58.6 | 58.7 | 58.7 | 43.6 |
| 24 | LB | 28.1 | 35.4 | 26.9 | 35.2 | 51.4 | 38.2 |
| 25 | PC | 50.8 | 53.6 | 57.2 | 53.5 | 53.4 | 51.4 |
| 26 | DC | 71.4 | 79.4 | 82.9 | 55.6 | 108.0 | 57.0 |
| 27 | RP | 69.6 | 68.7 | 69.2 | 73.0 | 111.3 | 77.6 |
| 29 | PB | 61.5 | 78.9 | 59.0 | 31.6 | 50.9 | 34.2 |
| 30 | RF | 31.8 | 38.8 | 41.3 | 22.0 | 30.0 | 33.3 |
| 31 | KP | 37.1 | 43.8 | 39.2 | 38.0 | 44.5 | 47.5 |
| 32 | LJ | 29.7 | 36.9 | 53.9 | 48.8 | 50.4 | 93.7 |
| 33 | RP | 33.9 | 33.2 | 28.4 | 27.0 | 46.0 | 49.8 |
| 34 | KM | 45.3 | 46.5 | 42.0 | 36.3 | 58.5 | 54.0 |
| 35 | JW | 44.1 | 58.6 | 41.3 | 37.7 | 33.1 | 42.0 |
| Average | — | 48.6 | 58.4 | 49.2 | 46.9 | 66.3 | 49.8 |
| SD | — | 17.3 | 34.5 | 17.4 | 18.9 | 47.9 | 20.0 |
| SEM | — | 3.0 | 6.0 | 3.0 | 3.3 | 8.3 | 3.5 |

TABLE 4

| | | OGX Light Weight Oil Benchmark | | Dexter Light Weight Oil | |
|---|---|---|---|---|---|
| Study ID | Initial | T1-T0 | T2-T0 | T1-T0 | T2-T0 |
| 1 | RH | −5.8 | 7.0 | 25.8 | 40.7 |
| 2 | WC | 7.5 | 2.2 | 11.6 | 6.5 |
| 3 | AC | 21.7 | −2.6 | 18.6 | 1.1 |
| 4 | PP | 7.1 | 5.4 | 6.4 | −6.7 |
| 5 | AM | −0.5 | −9.8 | 21.0 | 5.0 |
| 6 | DC | −8.9 | −3.5 | 0.7 | 3.7 |
| 7 | DE | 141.5 | −1.7 | 210.6 | 2.3 |
| 8 | MP | 9.8 | −5.5 | 12.1 | −6.0 |
| 9 | LF | 2.1 | 5.8 | 12.8 | −12.8 |
| 10 | MM | −0.6 | −4.8 | 18.4 | 6.2 |
| 11 | LR | 11.6 | 5.6 | −3.6 | −38.6 |
| 12 | LG | −2.7 | −4.9 | −7.0 | −13.3 |
| 13 | AB | 10.9 | 3.8 | 26.2 | −8.1 |
| 14 | JC | 9.1 | −6.0 | 8.8 | −10.0 |
| 15 | JT | 0.5 | −4.1 | −0.2 | −5.4 |
| 16 | KF | 6.7 | 0.3 | −5.8 | −3.1 |

TABLE 4-continued

| Study ID | Initial | OGX Light Weight Oil Benchmark | | Dexter Light Weight Oil | |
|---|---|---|---|---|---|
| | | T1-T0 | T2-T0 | T1-T0 | T2-T0 |
| 17 | JJ | −1.0 | −5.4 | 29.1 | 4.7 |
| 18 | DM | −2.0 | −5.7 | 16.1 | 36.7 |
| 19 | MH | 18.4 | −15.6 | 21.6 | −3.5 |
| 20 | RD | 11.1 | −7.3 | 19.9 | −21.9 |
| 22 | AM | 21.5 | 17.1 | 17.3 | 11.9 |
| 23 | NS | −3.9 | 2.1 | 0.0 | −15.1 |
| 24 | LB | 7.3 | 8.8 | 16.2 | 3.0 |
| 25 | PC | 2.9 | 6.4 | 0.0 | −2.1 |
| 26 | DC | 8.1 | 11.6 | 52.3 | 1.3 |
| 27 | RP | −0.9 | −0.4 | 38.3 | 4.6 |
| 29 | PB | 17.4 | −2.5 | 19.3 | 2.7 |
| 30 | RF | 7.1 | 9.6 | 8.0 | 11.3 |
| 31 | KP | 6.8 | 2.2 | 6.5 | 9.5 |
| 32 | LJ | 7.2 | 24.2 | 1.6 | 44.9 |
| 33 | RP | −0.7 | −5.5 | 19.0 | 22.8 |
| 34 | KM | 1.2 | −3.3 | 22.2 | 17.7 |
| 35 | JW | 14.5 | −2.8 | −4.6 | 4.3 |
| Average | — | 9.8 | 0.6 | 19.4 | 2.9 |
| SD | — | 24.8 | 8.0 | 36.7 | 16.8 |
| SEM | — | 4.3 | 1.4 | 6.4 | 2.9 |

Overall Performance

Light Oil composition of the invention was compared to Light Oil Benchmark. In Summary Light Oil composition of the invention,
- Has superior sensory performance in comparison to Light Oil Benchmark in providing good substantivity and moisturization on both bleached hair and Brazilian curly hair. Additionally, it provides significantly more smoothness and strongly preferred on Brazilian curly hair
- Provided significantly long-lasting shine over Light Oil Benchmark
- Exhibited excellent anti-frizz benefits when compared to Light Oil Benchmark and holds significantly better definition of the curls even after exposure to high humidity
- Imparted significantly better smoothness/suppleness over Light Oil Benchmark which agrees with sensory evaluation
- Provided significantly lower hair breakage and less split-ends when compared to Light Oil Benchmark Sensory Evaluation Preparation of Hair Tresses Hair tresses used for this study were 2 g/15 cm, medium bleached (5% hydrogen peroxide, pH ~9.43 for 15 minutes) caucasian dark brown hair and virgin Brazilian curly hair. All the tresses were pre-cleansed with 12% sodium laureth sulfate (SLES), pH 6.5 prior to the sensory evaluation. All assessments were performed in an air-conditioned room with a temperature of 21±1° C. and relative humidity of 50±3%.

Product Treatment

Each hair tress was wet for 30 sec (1 ltr/min at 35° C.) and then dried to approximately 30% residual water content. 50 μl of the oil was massaged onto the hair from root to tip and combed once for even distribution. After applying the oils, the treated hair strands were tested in a pairwise comparison using thirteen trained panelists. Every panelist was given their own pair of the hair tresses (Reference/Test Product) for comparison.

After Wet hair assessment, every tress was combed three times with coarse side of the comb. Hair was dried for 1 hour at 50° C. after which hair was assessed for dry hair properties.

Sensory Assessment

Parameters assed for Wet and Dry hair properties are listed below:

Wet Hair Properties Assessed:
- Combing with Coarse Side (1×)
- Combing with Fine Side (3×)
- Shine
- Coated (Substantive)
- Residues (Weightless)
- Slip
- Oiliness
- Acceptance Dry Hair Properties Assessed:
- Care before Combing (Visual)
- Volume before Combing (Visual)
- Frizz before Combing (Visual)
- Shine before Combing (Visual)
- Combing with Coarse Side (1×)
- Combing with Fine Side (3×)
- Volume after Combing
- Frizz after Combing
- Shine after Combing
- Oiliness (Visual)
- Oiliness
- Residues (Weightless)
- Coasted (Substantive)
- Glide
- Softness
- Smoothness
- Suppleness
- Moisturized
- Care Feel
- Acceptance
- Shine Preparation of Hair Tresses Hair tresses used for this method were 1" inch wide, 3 g/15 cm medium bleached (5% hydrogen peroxide, pH ~9.43 for 15 minutes) caucasian dark brown hair. All the tresses were pre-cleansed with 12% SLES, pH 6.5 prior to the test. All assessments were performed in an air-conditioned room with a temperature of 21±1° C. and relative humidity of 50±3%.

Product Treatment

200 μl (0.2 ml) of oil was applied for each hair tress. Oil was massaged onto the hair from root to tip and combed through for uniform distribution.

SAMBA System

SAMBA Hair system from Bossa Nova Vision, Los Angeles, CA, was used to measure shine on hair tresses. The system acquires images in parallel and crossed polarization state. Bossa Nova Technology Formula (LBNT) was used to evaluate shine (Lefaudeux et al., Third Annual Conference on Applied Hair Science, September 2008, http://www.spequation.com/files/journal-of-cosmetic-science-bossa-nova-tech-60-153-169-march-april-2009_5b45fb50b1be0.pdf):

$$LBNT = \frac{Sin}{(D + Sout) \times Wvisual}$$

D: is the total amount of diffused light
Sin: corresponds to the peak of specular light and contributes to increase in shine
Sout: corresponds to the wings of the specular light and contributes to decrease in shine
Wvisual: is the visual width of the distribution Nine (9) hair tresses were measured for each oil tested. Each tress is combed to realign the fibers and then placed on the combing cylinder to make the measurement. 5 replicated measurements are taken for every tress. This process is first done to get untreated values and then repeated after oil application. Shine measurements were taken immediately after treatment, after 1 hour, and after 24 hours. Percentage change in luster is calculated using the formula below $$\% \text{ Change in Luster} = \frac{L_{Treated} - L_{untreated}}{L_{untreated}} * 100$$

Anti-Frizz
Preparation of Hair Tresses

Mulatto curly 8" long rounded hair tresses were used for this method. All the tresses were pre-cleansed with 12% SLES, pH 6.5 prior to the test.
Product Treatment Each hair tress was wet for 30 sec (1 ltr/min at 35° C.), tresses were then combed and squeezed between two fingers to approximately 67% residual water content. 100 µl hair oil was applied on each damp tress with dyeing brush. After the application, tresses were then hung in a rack to dry overnight at 23° C. and 45% RH
Frizz Volume Each hair tress is hung in the volume-box by using a motorized hook. Once the software is initiated for every measurement, the hook turns in 720 steps. Five images are taken by a camera and the software calculates Frizz volume [cm3] from the images captured. FIG. 3 shows the imaging software. The region of interest for frizz volume is indicated in magenta color and volume is indicated in yellow.

Figure 4:
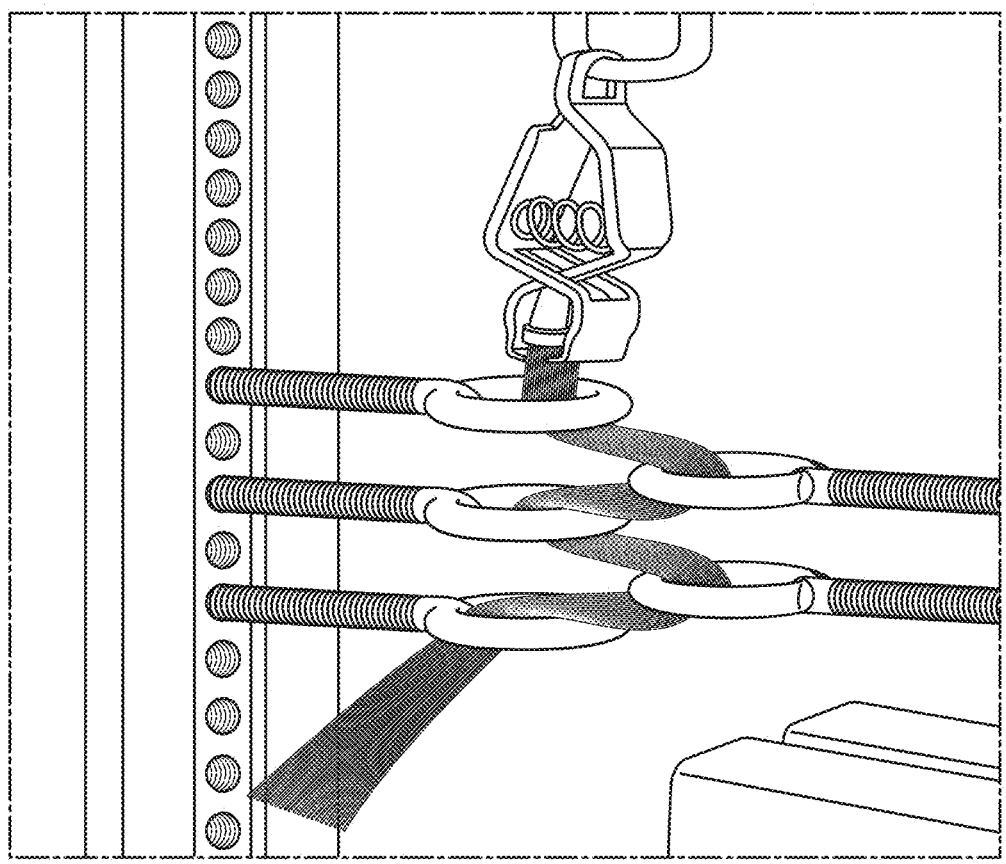
FIG. 4 is a photograph showing suppleness using a Zwick Roell testing machine, Kennesaw, GA.

Measurements are taken after drying (before combing), after combing with fine comb and after exposing the hair tresses to high humidity (1 h conditioning in a climate cabinet at 22° C./90% RH) for both the treatments.
Suppleness/Smoothness
Preparation of Hair Tresses Mulatto curly 8" long rounded hair tresses after frizz measurements were conditioned at 40% RH/22° C.
Suppleness Evaluation of maximum and mean resistance force to pull hair the strands through the loops using Zwick Machine was measured as shown in FIG. 4.
Anti-Breakage
Preparation of Hair Tresses Ten hair tresses (medium-dark brown Caucasian hair 12 cm/1 g) per sample were cleansed by incubation in 6% sodium lauryl ether sulfate (ac), pH 6.5, for 15 minutes, followed by rinsing and submerging three times in water for two minutes each. Finally, hair tresses were dried for 30 minutes hanging in a flow of warn air (approximately 55° C.). The preparation described was done by an automated system.
Product Treatment Wet hair tresses were treated with the formulation (0.50 µl product per 1 g hair). Hair tresses were dried for one hour lying on a grid above a fan blowing hot air (approximately 68° C.). After preparation, the hair strands were equilibrated for at least five hours at 30° C. and 40% relative humidity in the box of the automated combing device.
Repeated Combing of Hair Strands Hair tresses were combed 50,000 times (at 45 rpm). All evaluations were conducted at 30° C. and 40% relative humidity using an automated combing device as shown in FIG. 3.

After 50,000 combing strokes broken hair fibers were collected in drawers. Fibers longer than the diameter of the petri dish (about 9 cm) were sorted out, and the remaining fibers were weighed as shown in (FIG. 4). Hair breakage is quantified as ratio of weight of broken fibers to weight of the whole hair strand.

$$\text{Hair breakage } [\%] = \frac{\text{Weight of broken hair [g]}}{\text{Weight of complete hair strand [g]}}$$

Split-Ends

Images of hair strands after 50,000 combing strokes were characterized using Hirox KW-8700 digital microscope for split-ends at 500 µm and 1000 µm magnification.
Statistics
Sensory Evaluation To evaluate the sensory data, the medians for each parameter are calculated, as well as the average absolute deviation from the median as a measure of the variation of the individual values for each criterion. To calculate the statistical significance of a pair-wise comparison, the Wilcoxon test is carried out. In the charts, the position of the symbol indicates the median, and the average absolute deviation from the median is transformed into the weighted deviation from the median and shown in the chart in the form of shifted lines.
Shine/Anti-Frizz/Suppleness/Anti-Breaking Tukey's test was employed to compare difference between the products for all the methods except sensory evaluation. Tukey's test is a single-step multiple comparison procedure and statistical test used in conjunction with an ANOVA (analysis of variance) to find which means are significantly different from one another. The test compares the means of every treatment to the means of every other treatment. It is applied simultaneously to the set of all pair wise comparisons and identifies where the difference between two means is greater than the standard error expected to allow. The threshold of the test is the HSD-range (Honestly Significant Difference).

Figure 8:
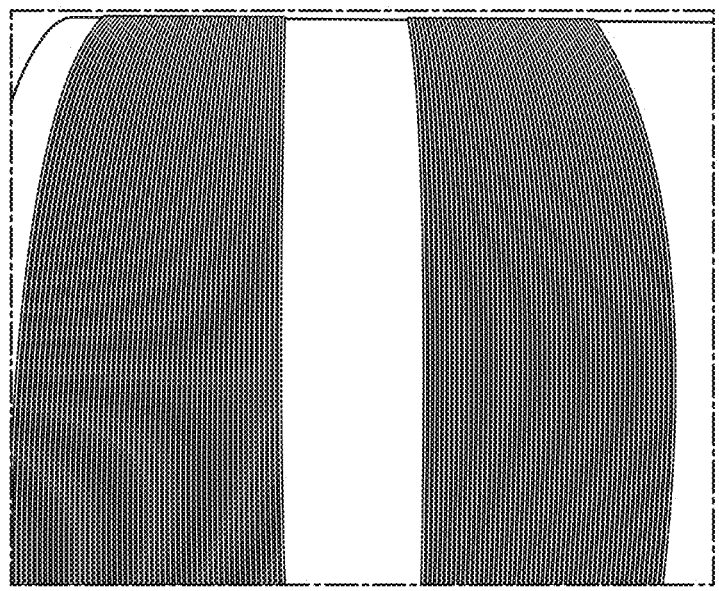
FIG. 8 is a photograph showing visual shine comparison of Light Oil composition of the invention with Light Oil Benchmark after 24 hrs.

The HSD-range is determined by the signal-to-noise ratio, and the number of measurements. The difference between two samples must be greater than the calculated HSD value to be significantly different at a 95% probability (P=0.05).
Results and Discussion
Sensory FIGS. 5 (a) (b) and FIGS. 6 (a) (b) shows the sensory comparison of Light Oil composition of the invention and Light Oil Benchmark on Medium bleached Caucasian and Brazilian curly Hair in wet and dry state respectively Light Oil composition of the invention performance in comparison to Light Oil Benchmark from FIGS. 5a and 5b:
  showed significantly less frizz before and after combing in dry state
  displayed significantly more shine in wet and dry state.
  significantly more substantive in wet and dry state
  significantly more moisturized in dry state
  showed significantly less weightless feel in both wet and dry state
  significantly less volume on hair in dry state Light Oil composition of the invention performance in comparison to Light Oil Benchmark from FIGS. 6a and 6b:
  showed significantly less frizz before and after combing in dry state
  displayed significantly more shine in wet and dry state.
  significantly more substantive in both wet and dry state significantly more smooth and supple in dry state
significantly made hair more moisturized and strongly preferred in dry state
showed significantly less weightless feel in both wet and dry state
significantly less volume on hair in dry state Shine FIGS. 7 and 8 shows the percentage change in luster comparing Light Oil composition of the invention and Light Oil Benchmark at different time points and visual shine comparison after 24 hrs, respectively.

Results showed:
Light Oil composition of the invention shows significantly higher shine immediately after application and provides long lasting shine up to 24 hours when compared to Light Oil Benchmark.
Higher luster from Light Oil composition of the invention is apparent to the naked eye even after 24 hours as show in FIG. 8.

Anti-Frizz

FIGS. 9 and 10 show frizz volume comparing Light Oil composition of the invention and Light Oil Benchmark at different treatment conditions and visual comparison of the hair tresses between the oil treatments respectively.

Results showed:
Frizz-volume of Light Oil composition of the invention is significantly lower than Light Oil Benchmark at every condition
Light Oil composition of the invention holds significantly better definition of the curls even after exposure to high humidity.

Suppleness/Smoothness

FIG. 11 shows Fmax (Maximum Force) and Fmean (Mean Force) to pull hair tresses through Zwick comparison between Light Oil composition of the invention and Light Oil Benchmark.

Results showed:
Smoothness/Suppleness of hair strands treated with Light Oil composition of the invention is significantly better than Light Oil Benchmark as indicated by Lower combing forces.

Anti-Breakage

FIG. 12 and FIG. 13 shows hair breakage [%] and split-ends comparison between Light Oil composition of the invention and Light Oil Benchmark, respectively.

Results showed:
Both Light Oil Benchmark and Light Oil composition of the invention significantly reduced hair breakage when compared to the untreated hair strands. Hair breakage produced by the strands treated with Light Oil composition of the invention was significantly lower in comparison to the Light Oil Benchmark.
Split-end quantification indicates that Light Oil composition of the invention shows less split-ends when compared to Light Oil Benchmark.

Additional Examples

After several iterations, the following formulations were selected for comparison testing:

| | | Penetrating Oil Composition of the Invention | |
|---|---|---|---|
| INCI | Trade Name | Penetrating Oil Benchmark | Penetrating Oil Composition of the Invention |
| Cyclotetrasiloxane | XIAMETER PMX-0244 Fluid | 35.00 | N/A |
| Cyclopentasiloxane (and) Dimethiconol | XIAMETER PMX 1501 Fluid | 60.50 | N/A |
| Isopropyl Myristate | Isopropyl Myristate | N/A | 22.42 |
| Dimethiconol in a low viscosity dimethicone fluid | XIAMETER PMX-1503 Fluid | N/A | 73.08 |
| C12-15 Alkyl Benzoate | Finsolv TN | 2.50 | 2.50 |
| Argania Spinosa (Argan) Kernel Oil | RITA Argan Oil | 1.50 | 1.50 |
| Fragrance | Fragrance | 0.50 | 0.50 |
| | Total | 100.00 | 100.00 |

| | | Serum Composition of the Invention | |
|---|---|---|---|
| INCI | Trade Name | OGX Nourishing + Coconut Milk Anti-Breakage Serum (91008) | DOW EXP-19-CB0327-2 (equivalent to Dexter Serum F#13589-127) |
| Cyclotetrasiloxane | XIAMETER PMX-0244 Fluid | 32.51 | N/A |
| Cyclopentasiloxane (and) Dimethiconol | XIAMETER PMX 1501 Fluid | 33.37 | N/A |
| Dimethicone | XIAMETER PMX-200 Fluid, 5 cst | N/A | 25.56 |
| Dimethiconol in a low viscosity Dimethicone fluid | XIAMETER PMX-1503 Fluid | N/A | 40.32 |

-continued

Serum Composition of the Invention

| INCI | Trade Name | OGX Nourishing + Coconut Milk Anti-Breakage Serum (91008) | DOW EXP-19-CB0327-2 (equivalent to Dexter Serum F#13589-127) |
|---|---|---|---|
| C12-15 Alkyl Benzoate | Finsolv TN | 1.00 | 1.00 |
| Fragrance | Fragrance | 0.12 | 0.12 |
| Dimethicone | Xiameter PMX 200 fl 350 cst; Ritasil 200 350 cst | 33.00 | 33.00 |
|  | Total | 100.00 | 100.00 |

Visual Comparison of Coated Hair Swatches

Prior to initialization testing 0.15 gm of sample/1 gram of hair was applied for each product and visually compared for evidence of oily residue or heaviness and pictures taken for comparison.

Figure 14A:
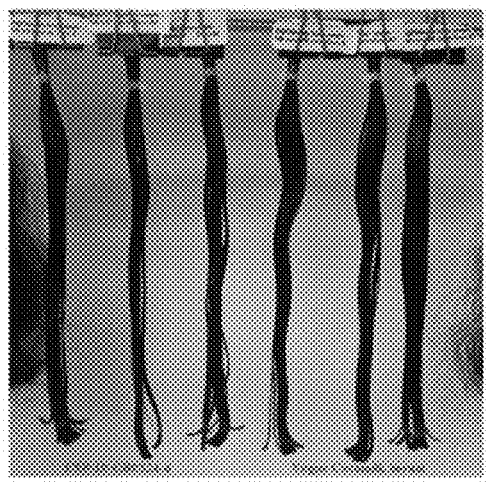
FIGS. 14a and 14b are images showing visual comparison of black hair treated with Serum composition of the invention v. Serum Benchmark (FIG. 14a) and Penetrating Oil composition of the invention v. Penetrating Oil Benchmark (FIG. 14b).
Figure 14B:
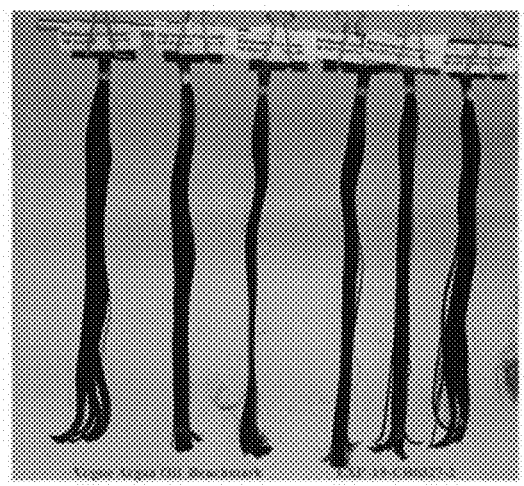
Figure 15A:
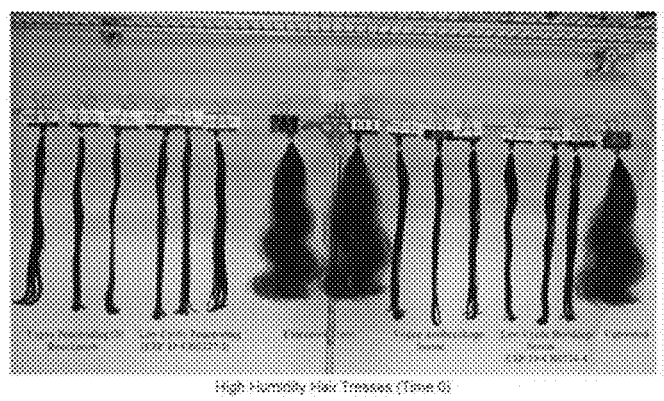
FIGS. 15a-15d are images showing visual comparison of frizzy black hair treated with Serum composition of the invention v. Serum Benchmark and Penetrating Oil composition of the invention v. Penetrating Oil Benchmark at T=0 (FIG. 15a); T=4 hours (FIG. 15b); .T=8 hours (FIG. 15c); and T=24 hours (FIG. 15d).
Figure 15B:
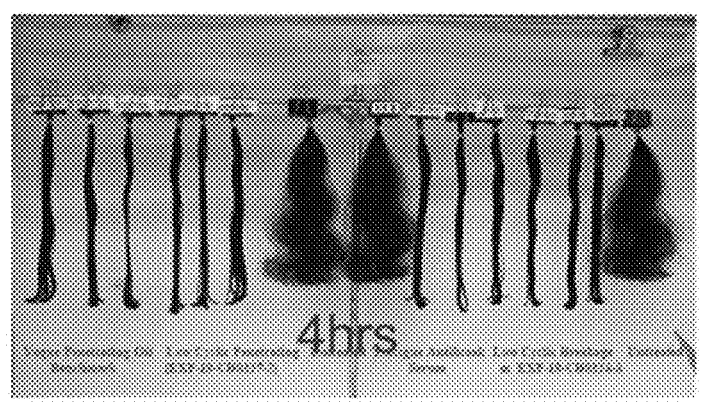
Figure 15C:
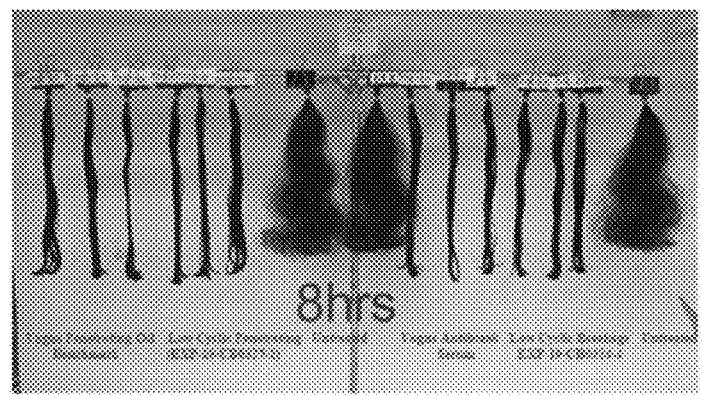
Figure 15D:
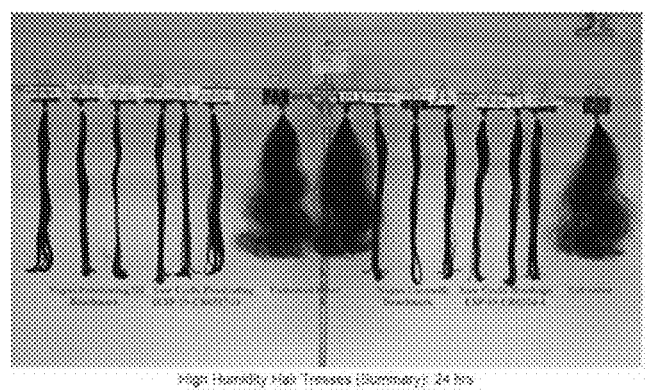
Figure 16:
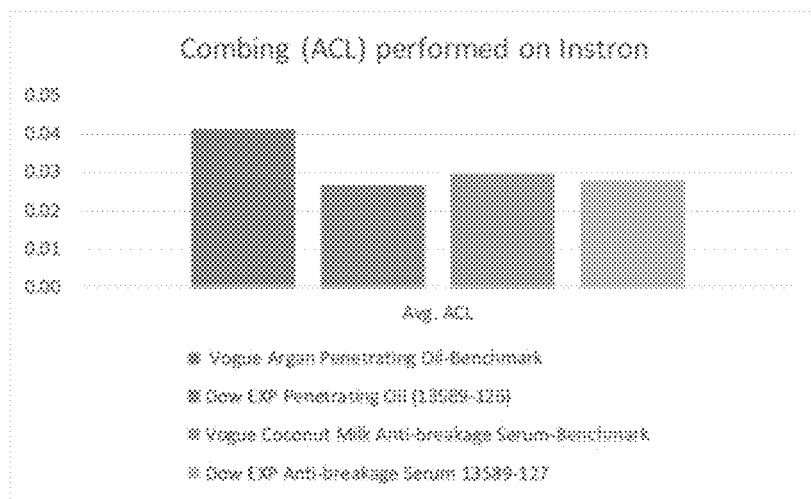
FIG. 16 is a graph showing combing values for Penetrating Oil Benchmark, Penetrating Oil composition of the invention, Serum Benchmark and Serum composition of the invention, as measured using an Instron tensile instrument.
Figure 17:
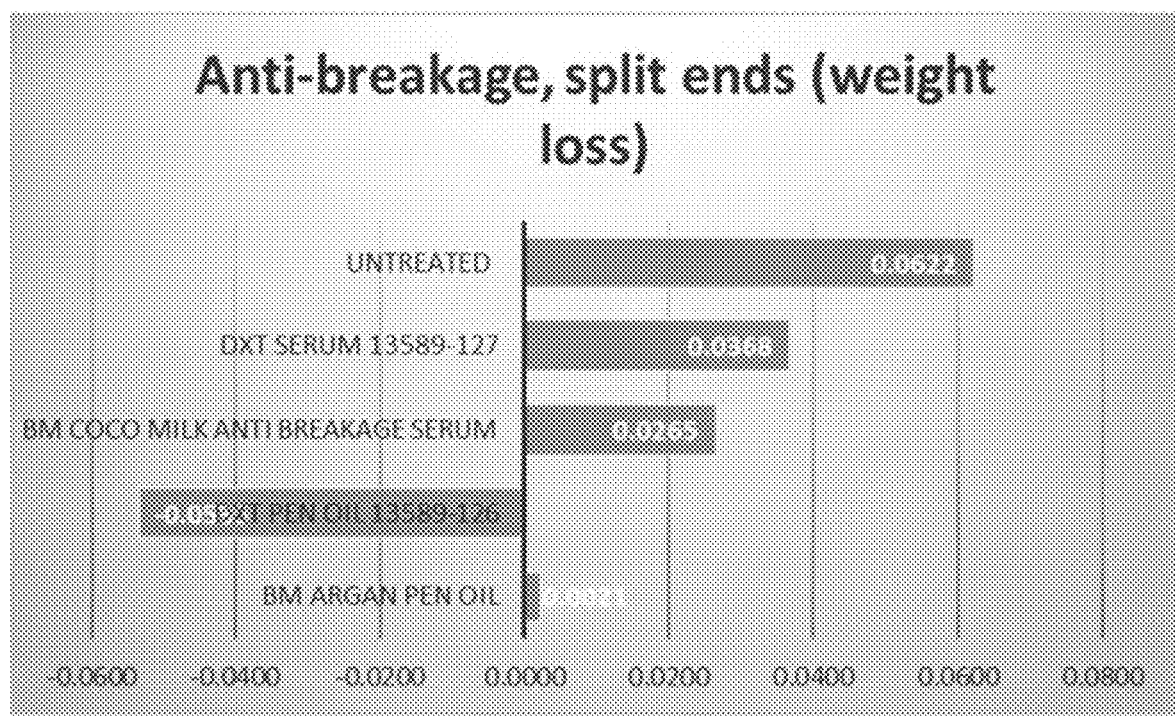
FIG. 17 is a graph showing anti-breakage values (as assessed via hair loss) for untreated hair, hair treated with Serum composition of the invention, Serum Benchmark, Penetrating Oil composition of the invention and Penetrating Oil Benchmark.
Figure 18A:
FIGS. 18a and 18b are images showing hair treated with Penetrating Oil composition of the invention v. Penetrating Oil Benchmark (FIG. 18a) and Serum composition of the invention v. Serum Benchmark (FIG. 18b), after combing.
Figure 18B:
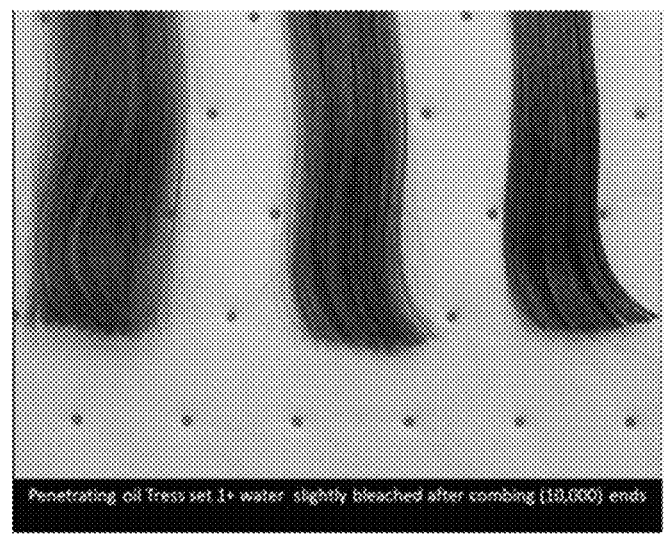
Figure 19:
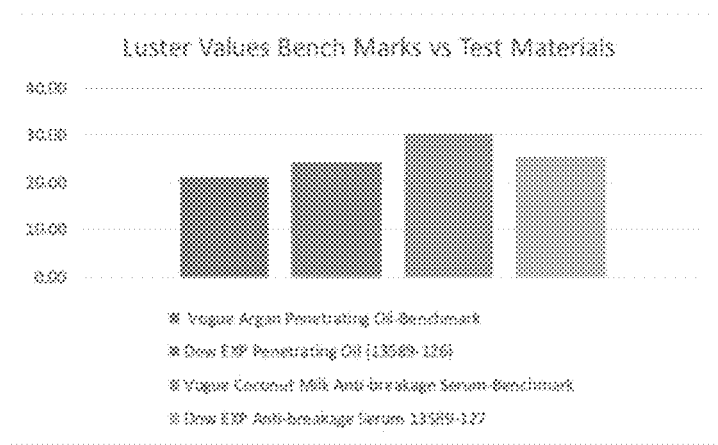
FIG. 19 is a graph showing luster values for Penetrating Oil Benchmark, Penetrating Oil composition of the invention, Serum Benchmark and Serum composition of the invention.
Figure 21A:
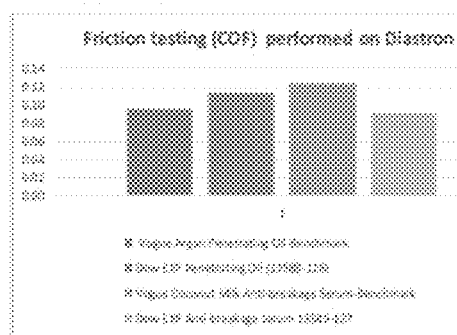
FIG. 21a and FIG. 21b are graphs showing coefficient of friction (CoF) for Penetrating Oil Benchmark, Penetrating Oil composition of the invention, Serum Benchmark and Serum composition of the invention with the cuticle (FIG. 21a) and against the cuticle (FIG. 21b).
Figure 21B:
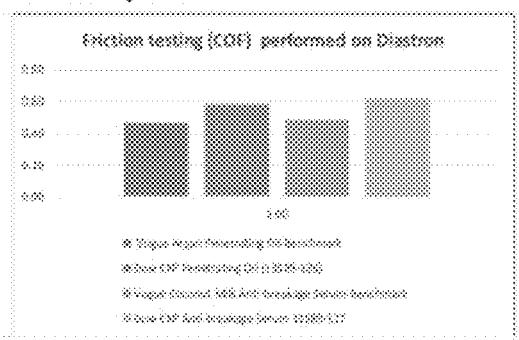

FIGS. 14a and 14b show that black hair tresses showed slight but not significant differences (likely due to differences in the volatile content of the formulations).

Frizz Control (Caucasian, Textured Hair)

Samples of frizzy black hair tresses were initially washed with a 1% sodium lauryl sulfate solution and treated with 0.4 gm treatment of the Benchmark or compositions of the invention per 2 gram tress (0.8 gram for 4 gram tress). These were allowed to dry for 18-24 hours and samples were placed at room temperature (25° C.) and high humidity (80%) for 24 hours and pictures taken at 0 hour, 4 hour, 8 hour, and the 24 hour timepoint (3 samples/test). FIGS. 15a-15d show that for samples of frizzy black hair, tresses were comparable.

Combing (Dry Combing Only)
1. Penetrating Oil composition of the invention vs Penetrating Oil Benchmark
2. Serum composition of the invention vs Serum Benchmark Antibreakage (resistance to breakage caused by brushing and styling)

Description: After treating, drying overnight, and acclimating to testing environment of 50% humidity and 23° C., hair tresses are weighed on an analytical scale to the fourth decimal. Hair is then fastened to a stationary rack in front of a cylinder with four combs attached. The cylinder rolls, pulling the combs through the hair at twenty RPM, with one rotation equaling four combing strokes, hair is run through 2500 cycles totaling 10,000 strokes. Hair is then removed and weighed on analytical balance to determine amount of hair lost.

Shine

Bossa Nova SAMBA Hair System test is used to determine the amount of luster coming from hair tresses treated with hair care formulations.

Treatment: 0.3 gm on a 2.5 gram tress. Dried overnight at 50% humidity and RT. Measured using an Bossa Nova SAMBA Hair System.

Tress Prep
 Rinse hair 15 s
 Apply for 30 s
  For Leave-On-apply 0.3-0.4 g/2 g tress, and do not rinse off
  For Rinse out-apply 0.8 g/2 g tress and rinse off for 30 s
 Let hair dry overnight.

Volume Down (for a more managed look) was assessed for the following:
1. Penetrating Oil composition of the invention vs Penetrating Oil Benchmark
2. Serum composition of the invention vs Serum Benchmark FIGS. 20a and 20b show that the compositions of the invention were comparable with "volume down" but had a slightly heavier appearance as compared to the respective benchmarks.

Friction Testing (CoF, Moisturization) was assessed on a Dia-stron hair friction instrument, Dia-stron Ltd., Andover, UK, for the following both with the cuticle and against the cuticle:
1. Penetrating Oil composition of the invention vs Penetrating Oil Benchmark
2. Serum composition of the invention vs Serum Benchmark Treatment: 0.1 g/g on slightly bleached hair Product Stability Penetrating Oil composition of the invention and Serum composition of the invention were placed on stability.
1. Samples of each composition were placed in glass under nominal ambient (i.e., 25° C./60% RH) and accelerated (45° C., 50° C./75% RH) storage conditions for 3-4 months. Additional samples were also subjected to freeze/thaw stability testing. No visible separation or syneresis was observed in any of the samples during this time.

Overall performance of the Penetrating Oil and Serum compositions of the invention were comparable to respective benchmarks, with the following observations:

The compositions of the invention perform at par or superior to benchmark by providing moisturized and substantive feel, long lasting shine, reduced frizz, and reduced hair breakage and split-ends.

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A leave-on light oil hair composition consisting of:
  about 12% of dimethicone, wherein the dimethicone comprises a linear silicone polymer having the molecular formula $C_8H_{24}O_2Si_3$; and
  about 88% of non-silicone ingredients including at least four selected from the group consisting of $C_{12-15}$ alkyl benzoate; coco-caprylate caprate; isododecene; octyldodecanol; isopropyl myristate; and propylheptyl caprylate; and combinations thereof, wherein the leave-on light oil hair composition comprises less than 15% water.

2. The leave-on light oil hair composition of claim 1, wherein the composition is free of cyclic silicone ingredients.

3. A method for controlling frizz of hair comprising applying the leave-on light oil hair composition of claim 1 to the hair.

4. A method for styling hair comprising applying the leave-on light oil hair composition of claim 1 to the hair.

5. A method for preventing damage of hair from surfactants comprising applying the leave-on light oil hair composition of claim 1 to the hair.

6. A method for promoting a healthy scalp of hair comprising applying the leave-on light oil hair composition of claim 1 to the hair.

7. A method for moisturizing hair and scalp comprising applying the leave-on light oil hair composition of claim 1 to the hair and scalp.

8. A method for increasing breakage resistance of hair comprising applying the leave-on light oil hair composition of claim 1 to the hair.

9. A method for increasing shine of hair comprising applying the leave-on light oil hair composition of claim 1 to the hair.

10. A method for increasing volume of hair comprising applying the leave-on light oil hair composition of claim 1 to the hair.

11. A method for reducing split ends of hair comprising applying the leave-on light oil hair composition of claim 1 to the hair.

12. A method for increasing curl definition of hair comprising applying the leave-on light oil hair composition of claim 1 to the hair.

13. A leave-on serum hair composition consisting of:
about 95% of dimethicone, wherein the dimethicone comprises a linear silicone polymer having the molecular formula $C_8H_{24}O_2Si_3$; and
about 5% of non-silicone ingredients including at least four of ingredients are selected from the group consisting of $C_{12-15}$ alkyl benzoate; coco-caprylate caprate; isododecene; octyldodecanol; isopropyl myristate; and propylheptyl caprylate; and combinations thereof,
wherein the leave-on light oil hair composition comprises less than 15% water.

14. The leave-on light oil hair composition of claim 13, wherein the composition is free of cyclic silicone ingredients.

* * * * *